US008951571B2

(12) United States Patent
Hammer et al.

(10) Patent No.: US 8,951,571 B2
(45) Date of Patent: Feb. 10, 2015

(54) POLYMER VESICLES FOR SELECTIVE ELECTROMAGNETIC ENERGY-INDUCED DELIVERY

(75) Inventors: Daniel A. Hammer, Villanova, PA (US); Ivan Julian Dmochowski, Philadelphia, PA (US); Gregory Patrick Robbins, Philadelphia, PA (US); Masaya S. Jimbo, Ann Arbor, MI (US); Michael J. Therien, Philadelphia, PA (US); Neha P. Kamat, Granger, IN (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 468 days.

(21) Appl. No.: 12/548,801

(22) Filed: Aug. 27, 2009

(65) Prior Publication Data

US 2010/0098773 A1    Apr. 22, 2010

Related U.S. Application Data

(60) Provisional application No. 61/100,472, filed on Sep. 26, 2008.

(51) Int. Cl.
| | | |
|---|---|---|
| *A61K 8/64* | (2006.01) | |
| *A61K 8/90* | (2006.01) | |
| *A61K 9/00* | (2006.01) | |
| *A61K 9/107* | (2006.01) | |
| *A61K 9/127* | (2006.01) | |

(52) U.S. Cl.
CPC ............. *A61K 9/0009* (2013.01); *A61K 9/1075* (2013.01); *A61K 9/1273* (2013.01)
USPC .......................................... 424/501; 424/499

(58) Field of Classification Search
None
See application file for complete search history.

(56) References Cited

U.S. PATENT DOCUMENTS

| | | | |
|---|---|---|---|
| 4,310,506 A | 1/1982 | Baldeschwieler et al. | |
| 4,350,676 A | 9/1982 | Laties et al. | |
| 4,515,736 A | 5/1985 | Deamer | |
| 4,522,803 A | 6/1985 | Lenk et al. | |
| 4,610,868 A | 9/1986 | Fountain et al. | |
| 4,891,043 A | 1/1990 | Zeimer et al. | |
| 6,835,394 B1 | 12/2004 | Discher et al. | |
| 7,217,427 B2 | 5/2007 | Discher et al. | |
| 2005/0019265 A1* | 1/2005 | Hammer et al. | 424/9.61 |
| 2007/0059245 A1* | 3/2007 | Young et al. | 424/9.34 |

FOREIGN PATENT DOCUMENTS

| | | |
|---|---|---|
| WO | WO 2005/016259 | 2/2005 |
| WO | WO 2007/038763 | 4/2007 |
| WO | WO 2007/081991 | 7/2007 |

OTHER PUBLICATIONS

Wajnberg et al. (Ferromagnetic resonance of horse spleen ferritin: core blocking and surface ordering temperatures, 153 J. Magnetic Resonance 69 (2001).*
Zhang et al. (Structure and activity of apoferritin-stabilized gold nanoparticles, 101 J. Inorg. Biochem. 1719 (2007)).*
Oxford English Dictionary defines "associate", accessed Aug. 12, 2013.*
Arifin et al., "Polymersome Encapsulated Hemoglobin: A Novel Type of Oxygen Carrier", Biomacromolecules, Jul.-Aug. 2005, 6(4), 2172-2181.
Bermudez et al., "Molecular Weight Dependence of Polymersome Membrane Structure, Elasticity, and Stability", Macromolecules, Oct. 8, 2002, 35(21), 8203-8208.
Bhargava et al., "Temperature-Induced Reversible Morphological Changes of Polystyrene-Block-Poly(Ethylene Oxide) Micelles in Solution", J. Am. Chem. Soc. Feb. 7, 2007, 129(5), 1113-1121.
Chasteen et al., "Mineralization in Ferritin: An Efficient Means of Iron Storage", J. Struct. Biol., Jun. 30, 1999, 126(3), 182-194.
Choi et al., "Artifical Organelle: ATP Synthesis From Cellular Mimetic Polymersomes", Nano Letters, Dec. 2005, 5(12), 2538-2542.
Christian et al., "Tat-Functionalized Near-Infrared Emissive Polymersomes for Dendritic Cell Labeling", Bioconjugate Chemistry, Jan.-Feb. 2007, 18(1), 31-40.
Discher et al., "Polymersomes: Tough Vesicles Made From Diblock Copolymers", Science, May 14, 1999, 284(5417), 1143-1146.
Discher et al., "Polymer Vesicles", Aug. 9, 2002, Science, 297(5583), 967-973.
Duncan et al., "Exceptional Near-Infrared Flourescence Quantum Yields and Excited-State Absorptivity of Highly Conjugated Porphyrin Arrays", J. Am. Chem. Soc., Jul. 19, 2006, 128(28), 9000-9001.
Evans, "New Membrane Concept Applied to the Analysis of Fluid Shear-and Micropipette-Deformed Red Blood Cells", Biophys. J., Sep. 1973, 13(9), 941-954.
Geng et al., "Hydrolytic Degradation of Poly(Ethylene Oxide)-Block-Polycaprolactone Worm Micelles", J. Am. Chem. Soc., Sep. 21, 2005, 127(37), 12780-12781.
Ghoroghchian et al., "Controlling Bulk Optical Properties of Emissive Polymersomes Through Intramembranous Polymer-Fluorophore Interactions", Chem. Mater., Feb. 17, 2007, 19(6), 1309-1318.

(Continued)

*Primary Examiner* — H. Sarah Park
(74) *Attorney, Agent, or Firm* — Baker & Hostetler LLP

(57) ABSTRACT

Provided are polymer vesicles comprising polymersomes, a radiofrequency absorbing moiety, a protein or a polysaccharide associated with the inner leaflet of the membrane and a therapeutic or diagnostic cargo. The invention also concerns the use of these polymer vesicles for selective electromagnetic energy-induced delivery of therapeutic or diagnostic agents.

14 Claims, 26 Drawing Sheets

(56) References Cited

OTHER PUBLICATIONS

Ghoroghchian et al., "Near-Infrared-Emissive Polymersomes: Self-Assembled Soft Matter for in Vivo Optical Imaging", Proc. Natl. Acad. Sci. USA, Feb. 22, 2005, 102(8), 2922-2927.

Ghoroghchian et al., "Quantitative Membrane Loading of Polymer Vesicles", Soft Matter, Sep. 20, 2006, 2, 973-980.

Hammer et al., "Leuko-Polymersomes", Faraday Discussions, 2008, 139, 129-141.

Harrison et al., "The Ferritins: Molecular Properties, Iron Storage Function and Cellular Regulation", BBA-Bioenergetics, Jul. 31, 1996, 1275(3), 161-203.

Hillmeyer et al., "Synthesis and Characterization of Model Polyalkane-Poly(ethylene oxide) Block Copolymers", Macromolecules, Oct. 21, 1996, 29(22), 6994-7002.

Jeong et al., "Cobalt-Filled Apoferritin for Suspended Single-Walled Carbon Nanotube Growth With Narrow Diameter Distribution", J. Am. Chem. Soc., Jun. 15, 2005, 127(23), 8238-8239.

Lee et al., "Preparation, Stability, and in Vitro Performance of Vesicles Made with Diblock Copolymers", Biotechnol. Bioeng., Apr. 20, 2001, 73(2), 135-145.

Meng et al., "Biodegradable Polymersomes as a Basis for Artificial Cells: Encapsulation, Release and Targeting", Journal of Controlled Release, Jan. 3, 2005, 101(1-3), 187-198.

Ortiz et al., "Computer Simulation of Aqueous Block Copolymer Assemblies: Length Scales and Methods", J. Polym. Sci. Pol. Phys., Jul. 15, 2006, 44(14), 1907-1918.

Photos et al., "Polymer Vesicles in Vivo: Correlations With PEG Molecular Weight", Journal of Controlled Release, Jul. 31, 2003, 90(3), 323-334.

Qin et al., "Temperature-Controlled Assembly and Release From Polymer Vesicles of Poly(ethylene oxide)-Block-Poly(N-isopropylacrylamide)", Advanced Materials, Oct. 30, 2006, 18(21), 2905-2909.

Robbins et al., "Photoinitiated Destruction of Composite Porphyrin-Protein Polymersomes", J. Am. Chem. Soc., Mar. 25, 2009, 131(11), 3872-3874.

Santore et al., "Effect of Surfactant on Unilamellar Polymeric Vesicles: Altered Membrane Properties and Stability in the Limit of Weak Surfactant Partitioning", Langmuir, Aug. 29, 2002, 18(20), 7299-7308.

Simsek et al., "Magic Ferritin: A Novel Chemotherapeutic Encapsulation Bullet", J. Magnetism and Magnetic Materials, May 2005, 293(1), 509-513.

Theil, "Ferritin: At the Crossroads of Iron and Oxygen Metabolism", Journal of Nutrition, May 2003, 133(5 Suppl. 1), 1549S-1553S.

Vieira et al., "Aggregation Behavior of Hydrophobically Modified Dextran in Aqueous Solution: A Florescence Probe Study", Carbohydrate Polymers, Aug. 1, 2003, 53(2), 137-143.

Webb et al., "Molecular Entrapment of Small Molecules Within the Interior of Horse Spleen Ferritin", Arch. Biochem. Biophys., Feb. 15, 1994, 309(1), 178-183.

* cited by examiner

A

B

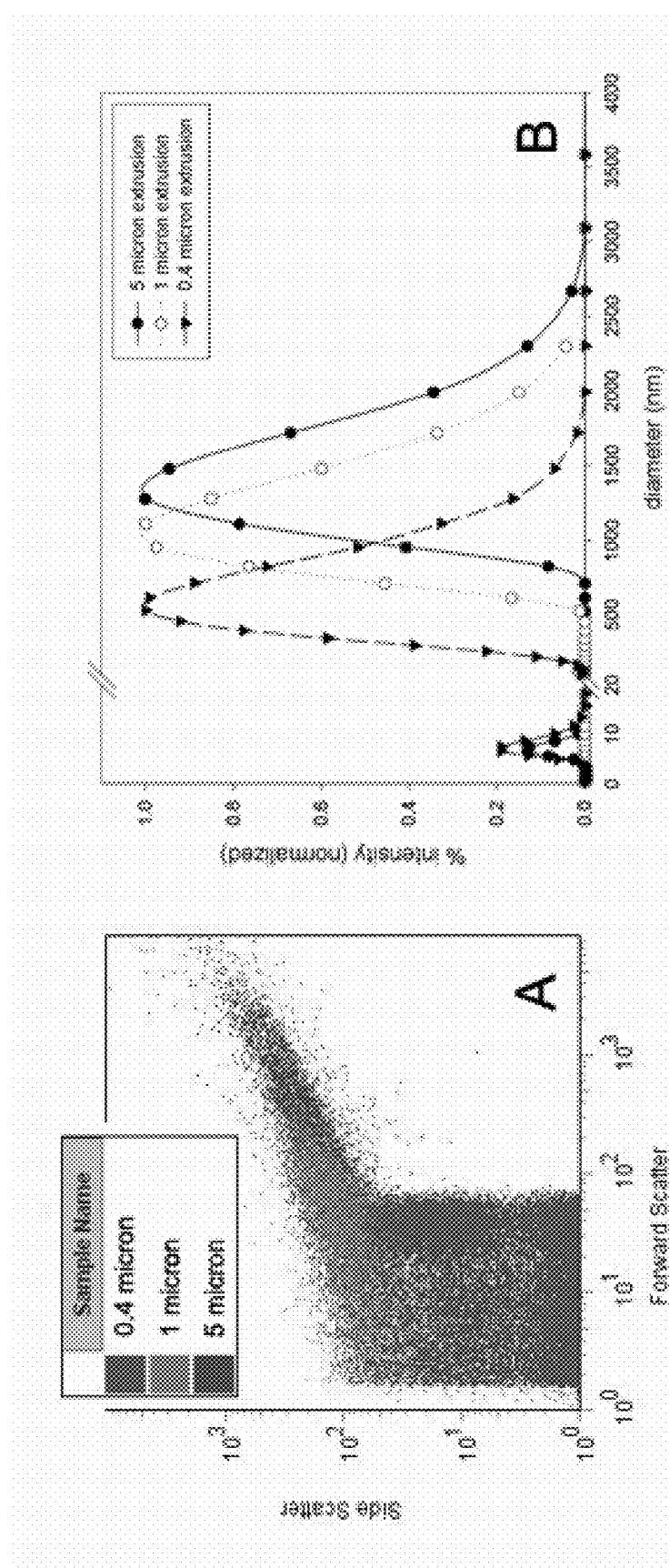
Figure 8A-B

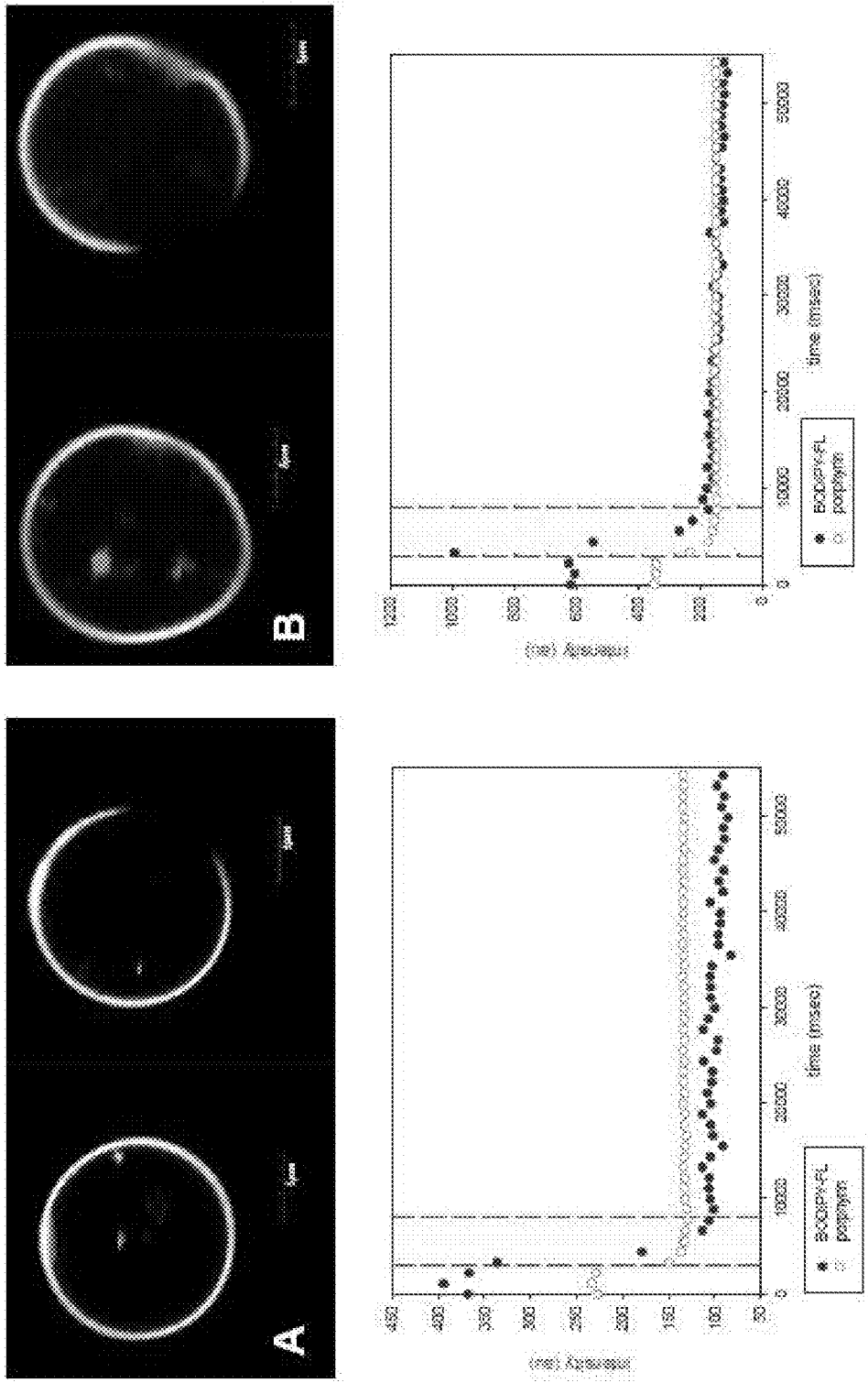
Figure 16A-B

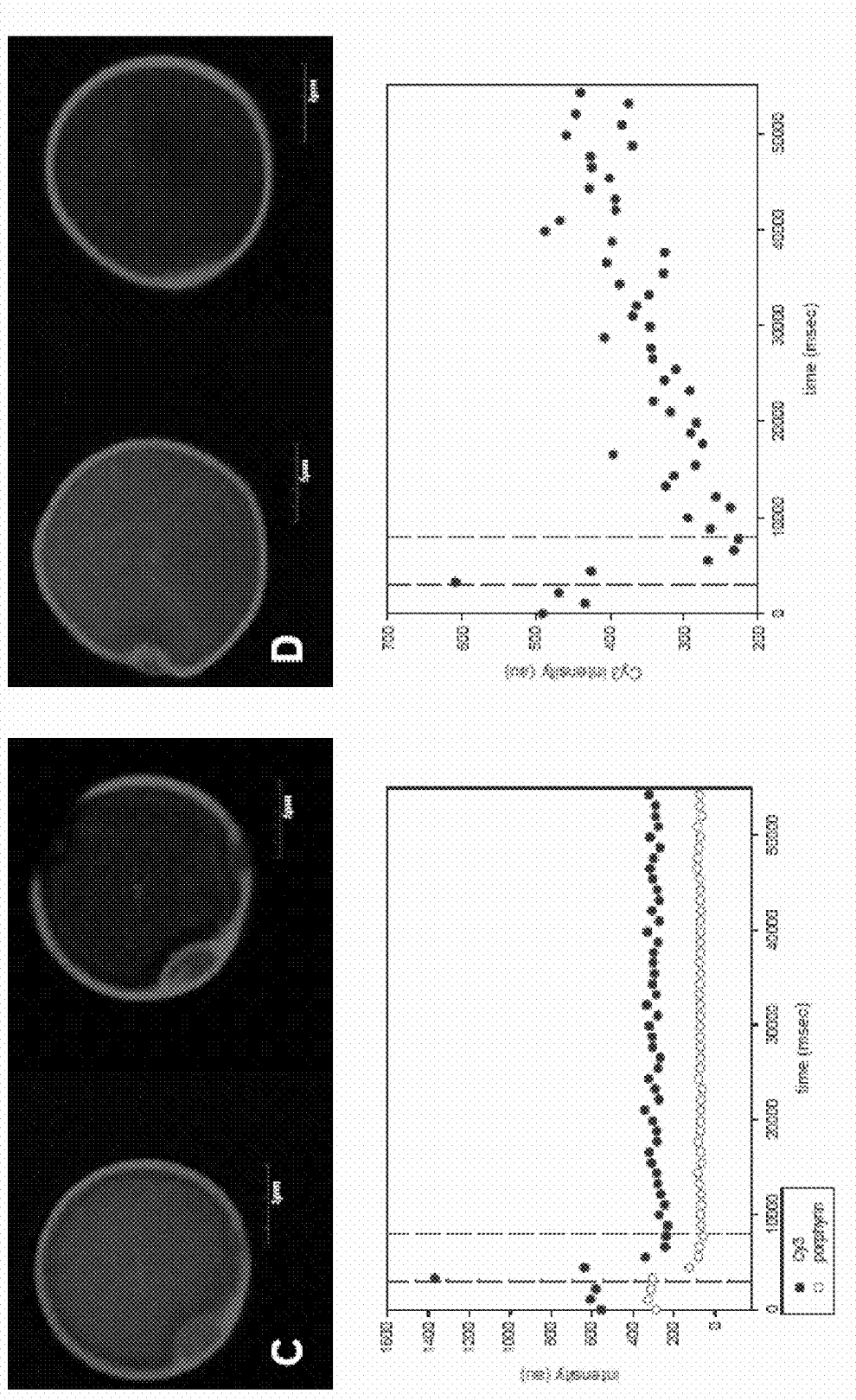
Figure 16C-D

Figure 16E-F
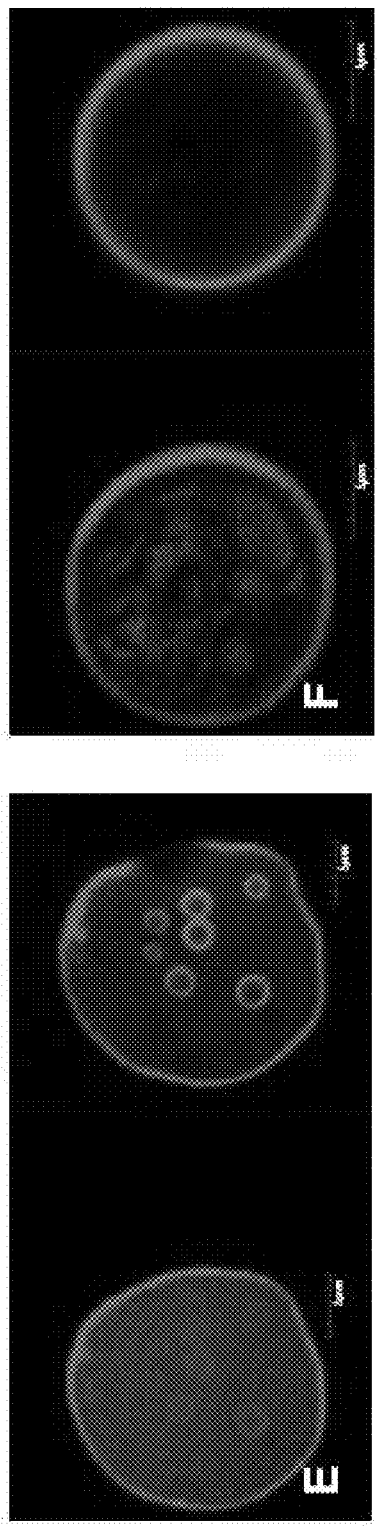
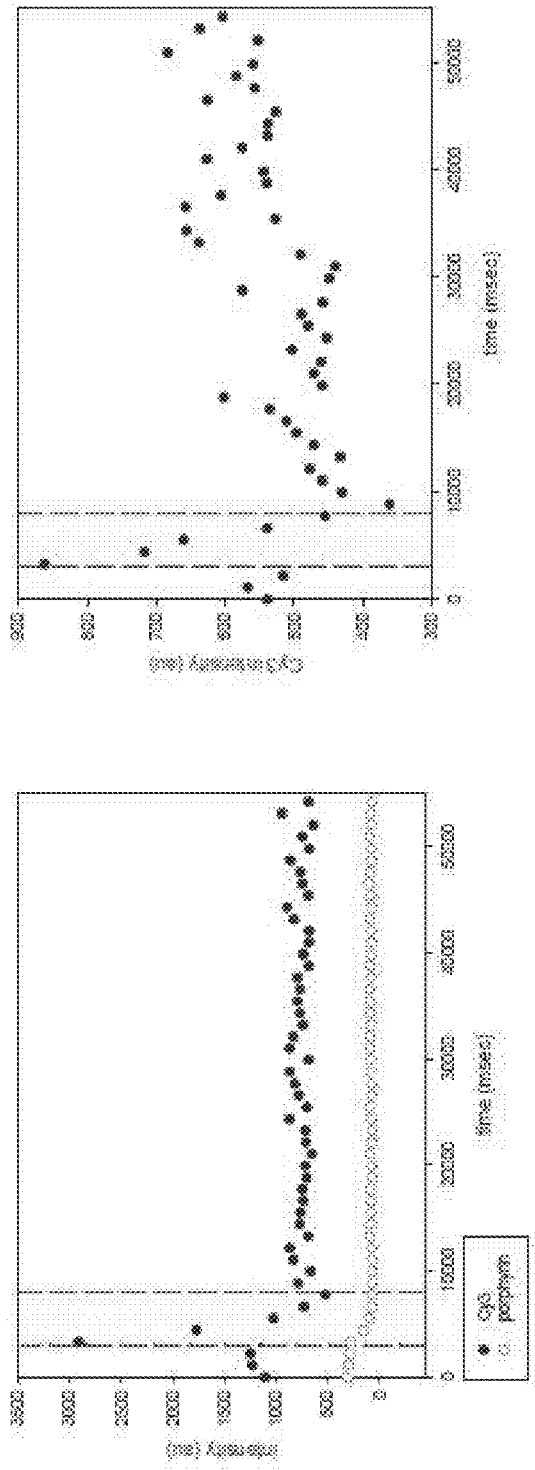

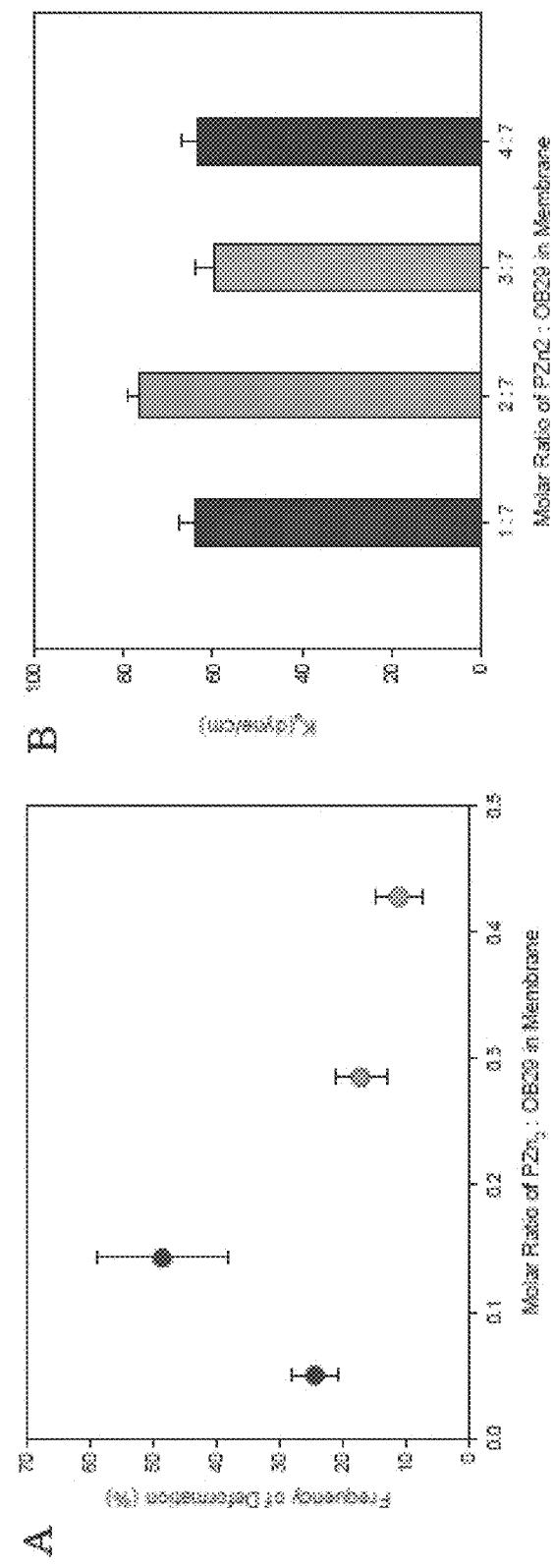
Figure 21A-B

POLYMER VESICLES FOR SELECTIVE ELECTROMAGNETIC ENERGY-INDUCED DELIVERY

CROSS REFERENCE TO RELATED APPLICATION

This application claims the benefit of U.S. Provisional Application No. 61/100,472 filed Sep. 26, 2008, which is incorporated by reference herein in its entirety.

STATEMENT OF FEDERALLY SPONSORED RESEARCH

This invention was made with Government support under Grant Nos. NSF MRSEC DMR-0520020 (to Ivan J. Dmochowski, Daniel A. Hammer, and Michael J. Therien), NSF CAREER CHE-0548188 and NCRR 1S10-RR-021113-01 (to Ivan J. Dmochowski), and National Institutes of Health Grant Nos. R01CA115229 and EB003457 (to Michael J. Therien and Daniel A. Hammer). The Government has certain rights in this invention.

FIELD OF THE INVENTION

The invention pertains to polymer vesicles for selective electromagnetic energy-induced delivery of therapeutic and diagnostic agents.

BACKGROUND OF THE INVENTION

Polymersomes, 50 nm-50 µm diameter vesicles formed from amphiphilic block copolymers, have attracted much attention due to their superior mechanical stabilities and unique chemical properties when compared to conventional lipid-based vesicles (liposomes) and micelles. (See, generally, Discher, D. E.; Eisenberg, A. *Science,* 2002, 297, 967-973; Discher, B. M.; Won, Y. Y.; Ege, D. S.; Lee, J. C. M.; Bates, F. S.; Discher, D. E.; Hammer, D. A. *Science* 1999, 284, 1143-1146; Lee, J. C. M.; Bermudez, H.; Discher, B. M.; Sheehan, M. A.; Won, Y. Y.; Bates, F. S.; Discher, D. E. *Biotechnol. Bioeng.* 2001, 73, 135-145, Bermudez, H.; Brannan, A. K.; Hammer, D. A.; Bates, F. S.; Discher, D. E., *Macromolecules* 2002, 35, 8203-8208, and Ghoroghchian, P. P.; Frail, P. R.; Susumu, K.; Blessington, D.; Brannan, A. K.; Bates, F. S.; Chance, B.; Hammer, D. A.; Therien, M. J. *P NATL ACAD SCI USA,* 2005, 102, 2922-2927.) Polymersomes are typically stronger than liposomes, have greater membrane thickness, and can be heavily PEGylated. (Discher, B. M.; Won, Y. Y.; Ege, D. S.; Lee, J. C. M.; Bates, F. S.; Discher, D. E.; Hammer, D. A. *Science,* 1999, 284, 1143-1146, Bermudez, H.; Brannan, A. K.; Hammer, D. A.; Bates, F. S.; Discher, D. E. *Macromolecules,* 2002, 35, 8203-8208.) Polymer vesicles have further proven capable of not only entrapping water-soluble hydrophilic compounds (drugs, vitamins, fluorophores, etc.) inside of their aqueous cavities but also hydrophobic molecules within their thick lamellar membranes. For instance, bacteriorhodopsin, ATP synthase, and hemoglobin have all been reconstituted within the aqueous core. (Choi, H. J.; Montemagno, C. D. *Nano Letters,* 2005, 5, 2538-2542, Arifin, D. R.; Palmer, A. F. *Biomacromolecules,* 2005, 6, 2172-2181.) Within the hydrophobic membrane, a variety of porphyrin-derived fluorophores have been incorporated at very high dye loadings, delivered intravenously to mice, and observed by in vivo fluorescence imaging. (Ghoroghchian, P. P.; Lin, J. J.; Brannan, A. K.; Frail, P. R.; Bates, F. S.; Therien, M. J.; Hammer, D. A. *Soft Matter,* 2006, 2, 973-980, Ghoroghchian, P. P.; Frail, P. R.; Susumu, K.; Blessington, D.; Brannan, A. K.; Bates, F. S.; Chance, B.; Hammer, D. A.; Therien, M. J. *P NATL ACAD SCI USA,* 2005, 102, 2922-2927, Christian, N. A.; Milone, M. C.; Ranka, S. S.; Li, G. Z.; Frail, P. R.; Davis, K. P.; Bates, F. S.; Therien, M. J.; Ghoroghchian, P. P.; June, C. H.; Hammer, D. A. *Bioconjugate Chemistry,* 2007, 18, 31-40.) Moreover, the size, membrane thickness, and stabilities of these synthetic vesicles can be rationally tuned by selecting block copolymer chemical structure, number-average molecular weight, hydrophilic to hydrophobic volume fraction, and via various preparation methods. (See Bhargava, P.; Tu, Y. F.; Zheng, J. X.; Xiong, H. M.; Quirk, R. P.; Cheng, S. Z. D. *J. Am. Chem. Soc.* 2007, 129, 1113-1121, Ortiz, V.; Nielsen, S. O.; Klein, M. L.; Discher, D. E. *J POLYM SCI POL PHYS,* 2006, 44, 1907-1918.) Polymersomes thus have many attractive characteristics that lend to their potential application in medical imaging, drug delivery, and cosmetic devices. (See, Discher, D. E.; Eisenberg, A. *Science,* 2002, 297, 967-973, Frail, P. R.; Susumu, K.; Blessington, D.; Brannan, A. K.; Bates, F. S.; Chance, B.; Hammer, D. A.; Therien, M. J. *P NATL ACAD SCI USA,* 2005, 102, 2922-2927 and Meng F.; Engbers, G. H. M.; Feijen J. *Journal of Controlled Release,* 2005, 101, 187-198.)

Lisposomes have been studied as delivery systems for therapeutic agents. (U.S. Pat. No. 4,891,043.) Early studies described the use of heat to release material encapsulated in lipid vesicles. Microwaves have been applied to heat specific tissue areas after the injection of heat-sensitive lipid vesicles. The major drawback of the use of microwaves is that microwaves cannot be focused as they have long wavelengths, and therefore they tend to damage surrounding tissues. In addition, microwaves indiscriminately heat up both the liposomes and the surrounding tissues, and since microwaves are non-visible electromagnetic energy they cannot be aimed at the target tissues accurately. The use of lipid vesicles for delivery of material in the body is disclosed in several patents. (U.S. Pat. No. 4,310,506 to Baldeschwieler et al; U.S. Pat. No. 4,350,676 to Laties et al; U.S. Pat. No. 4,515,736 to Deamer; U.S. Pat. No. 4,522,803 to Lenk et al.; and U.S. Pat. No. 4,610,868 to Fountain et al.) Due to the drawbacks of employing microwave energy, the use of laser light to rupture lipid vesicles was studied. The use of a system employing a laser to rupture laser light-absorbing and heat-sensitive lipid vesicles which thereby release the drugs or dyes encapsulated therein is disclosed in U.S. Pat. No. 4,891,043 to Zeimer et al.

The drawback of employing lipid vesicles for intracorporeal delivery of therapeutic agents is that lipid vesicles lack strength and durability. Researchers have turned to polymer vesicles as favored candidates for targeted delivery of therapeutic agents. Pioneering efforts to manipulate the morphology of polymer vesicles using external stimuli have recently been described including reversible, temperature-dependent vesicles which interchange between morphologies. (Geng, Y.; Discher, D. E. *J. Am. Chem. Soc.,* 2005, 127, 12780-12781, Qin, S. H.; Geng, Y.; Discher, D. E.; Yang, S. *Advanced Materials,* 2006, 18, 2905, Bhargava, P.; Tu, Y. F.; Zheng, J. X.; Xiong, H. M.; Quirk, R. P.; Cheng, S. Z. D. *J. Am. Chem. Soc.,* 2007, 129, 1113-1121.) New methods for externally modulating polymersome structure and function would greatly expand the utility of these organic materials for applications in engineering and biomedicine.

PCT/US2006/038189, filed Sep. 28, 2006, teaches, inter alia, poly(ethyleneoxide)-b-polycaprolactone (PEO-b-PCL) diblock copolymers that are biodegradable and/or bioresorbable. PCT/US2007/00621, filed Jan. 10, 2007, teaches, inter alia, polymersomes containing multi[(porphinato)metal] compounds having proquinoidal spacer units. PCT/US2004/

024014, filed Jul. 26, 2004, discloses, among other things, polymersomes having photo-emissive agents dispersed within the polymersome membrane. PCT/US2004/024014 also teaches polymersomes having photo-emissive agents dispersed within the polymersome membrane. U.S. Pat. No. 6,835,394, issued on Dec. 28, 2004, is directed to polymersomes and related encapsulating membranes with extensive covalent cross-linking of the membrane, and methods of controlling release of the encapsulating material. U.S. Pat. No. 7,217,427, issued on May 15, 2007 sets forth, inter alia, polymersomes and related encapsulating membranes with extensive covalent cross-linking of the membrane, and methods of encapsulating material in the polymersome. All of these materials are incorporated herein by reference.

There remains a need for polymersomes that can respond selectively to an external stimulus in order to deliver a cargo to target cells or tissues. Such cargo may be therapeutic, analgesic, diagnostic or otherwise useful in the treatment, palliation or diagnosis of disease.

SUMMARY

Provided are polymer vesicles for intracorporeal administration comprising an encapsulating polymer membrane, and a radiofrequency absorptive moiety either forming part of the membrane or attached or conjugated to the membrane, preferably external to the lumen of the vesicle; said vesicle further comprising protein in the lumen of the vesicle and associated with the inner leaflet of the membrane; as well as a therapeutic or diagnostic cargo in the lumen of the vesicle.

Also disclosed are polymer vesicles for intracorporeal administration comprising at least one targeting moiety on the membrane external to the lumen. Polymer vesicles for intracorporeal administration are provided having radiofrequency absorptive material including one or more porphyrins.

In some compositions, the polymer membrane of the polymer vesicles is composed of amphiphilic block copolymer comprising at least one hydrophilic polymer bonded to at least one hydrophobic polymer.

Provided are compositions for intracorporeal administration comprising polymer vesicles wherein the polymer vesicles comprise an encapsulating polymer membrane, and a radiofrequency absorptive moiety either forming part of the membrane or attached or conjugated to the membrane external to the lumen of the vesicle; said vesicle further comprising protein in the lumen of the vesicle and associated with the inner leaflet of the membrane, and therapeutic or diagnostic cargo in the lumen of the vesicle in a pharmaceutically acceptable carrier or diluent. In some compositions for intracorporeal administration, the polymer vesicles further comprise at least one targeting moiety on the membrane external to the lumen.

Provided are methods for releasing a therapeutic or diagnostic material at a preselected site inside the body of a subject. The subject is first administered a composition comprising vesicles; wherein said vesicles comprise an encapsulating polymer membrane. Contained within the polymer membrane is a radiofrequency absorptive moiety, and internal to the polymersome there is a protein constraining the inner leaflet of the membrane. The vesicles further comprise a cargo internal to the polymersome. The selected site is then exposed with electromagnetic radiation effective for releasing said therapeutic or diagnostic agent from the vesicles.

In some aspects, the polymer vesicles further comprise at least one targeting moiety associated with a surface of the polymersome.

In further aspects of the invention, the electromagnetic radiation is selected to interact with the radiofrequency absorptive moiety to generate heat and said release is accompanied by budding of the vesicles. In certain preferred embodiments the radiofrequency absorptive material is a porphyrin. In further preferred embodiments the electromagnetic energy is laser radiation, while in other preferred embodiments the electromagnetic energy is fluorescent light. In other embodiments, the electromagnetic energy is the light emitted from a mercury arc lamp.

In some aspects, the protein in the lumen of the vesicle and associated with the inner leaflet of the membrane of the vesicle is ferritin, apoferritin, bovine serum albumin, a cytokine, myoglobin, hemoglobin or combinations thereof.

In further aspects of the invention the block copolymer is a polyethyleneoxide-polybutadiene block copolymer or a polyethyleneoxide-polycaprolactone block copolymer. In certain embodiments, the block copolymers are crosslinked. In other embodiments, the block copolymers are chemically crosslinked. In certain embodiments the block copolymer is chemically crosslinked by associating avidin with biotin attached to a terminal end of a polyethyleneoxide portion of the polyethyleneoxide-polycaprolactone block copolymer. In other embodiments, the block copolymer is chemically crosslinked by associating avidin with biotin attached to a terminal end of a polyethyleneoxide portion of the polyethyleneoxide-polybutadiene block copolymer.

Provided are polymer vesicles for intracorporeal administration comprising an encapsulating polymer membrane, and a radiofrequency absorptive moiety either forming part of the membrane or attached or conjugated to the membrane, preferably external to the lumen of the vesicle; said vesicle further comprising polysaccharide in the lumen of the vesicle and associated with the inner leaflet of the membrane; as well as a therapeutic or diagnostic cargo in the lumen of the vesicle.

In some aspects, the polysaccharide in the lumen of the vesicle and associated with the inner leaflet of the membrane of the vesicle is dextran, pectin, chitosan, pullulan, carboxymethylpullulan, dextrin, curdlan, levan, schizophyllan, or combinations thereof.

Provided are compositions for intracorporeal administration comprising polymer vesicles wherein the polymer vesicles comprise an encapsulating polymer membrane, and a radiofrequency absorptive moiety either forming part of the membrane or attached or conjugated to the membrane external to the lumen of the vesicle; said vesicle further comprising polysaccharide in the lumen of the vesicle and associated with the inner leaflet of the membrane, and therapeutic or diagnostic cargo in the lumen of the vesicle in a pharmaceutically acceptable carrier or diluent. In some compositions for intracorporeal administration, the polymer vesicles further comprise at least one targeting moiety on the membrane external to the lumen.

Provided are methods for releasing a therapeutic or diagnostic material at a preselected site inside the body of a subject. The subject is first administered a composition comprising vesicles; wherein said vesicles comprise an encapsulating polymer membrane. Contained within the polymer membrane is a radiofrequency absorptive moiety, and internal to the polymersome there is a protein constraining the inner leaflet of the membrane. The vesicles further comprise a cargo internal to the polymersome. The selected site is then exposed with electromagnetic radiation effective for releasing said therapeutic or diagnostic agent from the vesicles.

DETAILED DESCRIPTION

Figure 1:
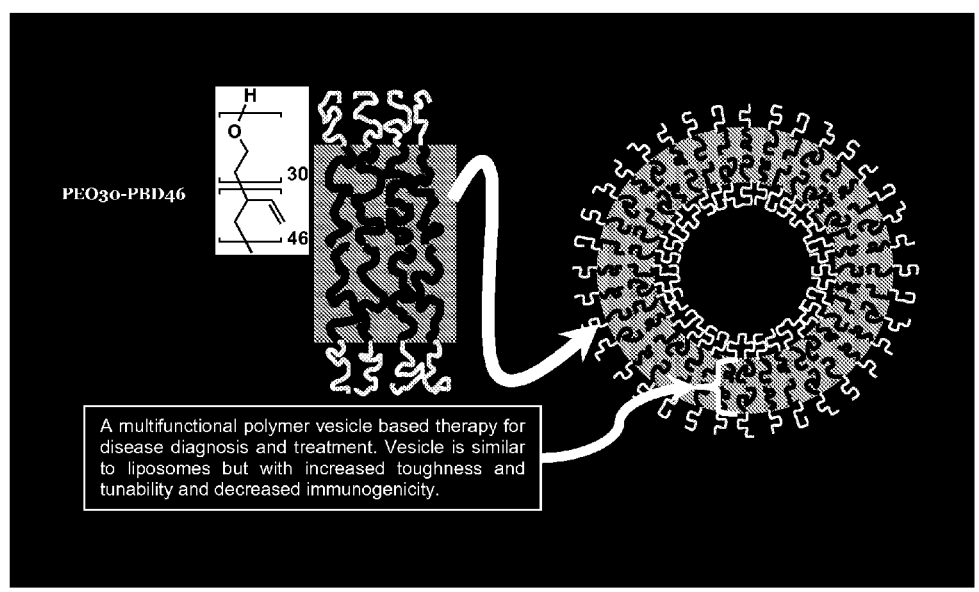
FIG. 1 illustrates a multifunctional polymer vesicle based therapy for disease diagnosis and treatment. Please note that FIG. 1 in the provisional application comprised a poster presentation which is incorporated herein by reference, however the figure has been simplified for clarity for the current non-provisional application.

Provided are polymer vesicles for intracorporeal administration comprising an encapsulating polymer membrane, and a radiofrequency absorptive moiety either forming part of the membrane or attached or conjugated to the membrane, preferably external to the lumen of the vesicle; said vesicle further comprising protein in the lumen of the vesicle and associated with the inner leaflet of the membrane; as well as a therapeutic or diagnostic cargo in the lumen of the vesicle.

Also disclosed are polymer vesicles for intracorporeal administration comprising at least one targeting moiety on the membrane external to the lumen. Polymer vesicles for intracorporeal administration are provided having radiofrequency absorptive material including one or more porphyrins.

In some compositions, the polymer membrane of the polymer vesicles is composed of amphiphilic block copolymer comprising at least one hydrophilic polymer bonded to at least one hydrophobic polymer.

Provided are compositions for intracorporeal administration comprising polymer vesicles wherein the polymer vesicles comprise an encapsulating polymer membrane, and a radiofrequency absorptive moiety either forming part of the membrane or attached or conjugated to the membrane external to the lumen of the vesicle; said vesicle further comprising protein in the lumen of the vesicle and associated with the inner leaflet of the membrane, and therapeutic or diagnostic cargo in the lumen of the vesicle in a pharmaceutically acceptable carrier or diluent. In some compositions for intracorporeal administration, the polymer vesicles further comprise at least one targeting moiety on the membrane external to the lumen.

Provided are methods for releasing a therapeutic or diagnostic material at a preselected site inside the body of a subject. The subject is first administered a composition comprising vesicles; wherein said vesicles comprise an encapsulating polymer membrane. Contained within the polymer membrane is a radiofrequency absorptive moiety, and internal to the polymersome there is a protein constraining the inner leaflet of the membrane. The vesicles further comprise a cargo internal to the polymersome. The selected site is then exposed with electromagnetic radiation effective for releasing said therapeutic or diagnostic agent from the vesicles.

In some aspects, the polymer vesicles further comprise at least one targeting moiety associated with a surface of the polymersome.

In further aspects of the invention, the electromagnetic radiation is selected to interact with the radiofrequency absorptive moiety to generate heat and said release is accompanied by budding of the vesicles. In certain preferred embodiments the radiofrequency absorptive material is a porphyrin. In further preferred embodiments the electromagnetic energy is laser radiation, while in other preferred embodiments the electromagnetic energy is fluorescent light. In other embodiments, the electromagnetic energy is the light emitted from a mercury arc lamp.

In some aspects, the protein in the lumen of the vesicle and associated with the inner leaflet of the membrane of the vesicle is ferritin, apoferritin, bovine serum albumin, a cytokine, myoglobin, hemoglobin, or combinations thereof.

In further aspects of the invention the block copolymer is a polyethyleneoxide-polybutadiene block copolymer or a polyethyleneoxide-polycaprolactone block copolymer. In certain embodiments, the block copolymers are crosslinked. In other embodiments, the block copolymers are chemically crosslinked. In certain embodiments the block copolymer is chemically crosslinked by associating avidin with biotin attached to a terminal end of a polyethyleneoxide portion of the polyethyleneoxide-polycaprolactone block copolymer. In other embodiments, the block copolymer is chemically crosslinked by associating avidin with biotin attached to a terminal end of a polyethyleneoxide portion of the polyethyleneoxide-polybutadiene block copolymer.

In some aspects, the invention concerns polymersomes that release their cargo in response to electromagnetic energy or sound. In some embodiments, the invention concerns polymersomes composed of amphiphilic block copolymers that include a radiofrequency absorptive moiety in their hydrophobic membranes, and a protein in the lumen of the vesicle and associated with the inner leaflet of the membrane. In some preferred embodiments the radiofrequency absorptive material is a porphyrin. Such polymersomes respond to irradiation with electromagnetic energy by undergoing morphological changes that range from budding to total polymersome destruction. Budding may be observed using CSLM. Budding is the division of a single vesicle into two more individual vesicles or polymer structures and is indicative of disruption of the polymersome membrane. Such polymersomes may also be loaded with therapeutic or diagnostic agents and are stimulated to release their cargo in response to electromagnetic energy or sound. Budding is then indicative of cargo release by the polymersomes. In some preferred embodiments the electromagnetic energy is laser radiation. In other preferred embodiments the electromagnetic energy is a fluorescent lamp. These polymersomes may be used to deliver therapeutic or diagnostic agents through the bloodstream or through topical application to selective sites in the body that may be irradiated by the electromagnetic energy. For example, the blood vessels in the retina of the eye, the vitreous inside the eye, the skin, larynx, uterus, stomach, or other portions of the gastrointestinal tract or other tissues of the body that may be exposed to electromagnetic energy are candidates for treatment using this system. The electromagnetic energy may be applied in various forms. For example, it may be applied in the form of a laser beam directed to the target tissue, or it may be in the form of light emitted by a fluorescent lamp. Endoscopy, colonoscopy, laparoscopy or other medical techniques may be employed to bring the target tissue in contact with the electromagnetic energy.

Polymersomes are roughly spherical, hollow vesicles comprising a hydrophobic shell, an aqueous core, and inner and outer surfaces comprising hydrophilic branches. Polymersomes have diameters in the range of from about 50 nm to about 50 µm. Polymersomes are conveniently made, for example, using amphiphilic synthetic block copolymers to form the vesicle membrane. Amphiphilic diblock or multi-block copolymers may be used to form thick-walled vesicles when placed in aqueous media. Polymersomes can be stably prepared by a number of techniques which are common to liposomes. (Lee et al., *Biotechnology and Bioengineering*, vol. 73, no. 2, Apr. 20, 2001.) Processes such as film rehydration, sonication, and extrusion can generate many-micron giant vesicles as well as monodisperse vesicles with diameters as small as 100 nanometers. Amphiphilic diblock copolymers generally have one block soluble in water, and the other block essentially water insoluble. The block soluble in water is known as the hydrophilic portion and the block insoluble in water is known as the hydrophobic portion. In some preferred embodiments the amphiphilic block copolymer comprises polyethylenedioxide-polybutadiene (PEO-PBD). In PEO-PBD the hydrophilic block is PEO and the hydrophobic block is PBD. In other preferred embodiments the amphiphilic block copolymer comprises polyethylenedioxide-polyethylethylene (PEO-PEE). PEO-PEE and PEO-PBD are known to form thick-walled (e.g., about 10 nm thick) vesicles that exhibit improved stability compared to liposomes. For example, a PEO-PEE diblock introduced by Hillmeyer and Bates, *Macromolecules,* 1996; 29:6994-7002, specifically $EO_{40}$-$EE_{37}$ (designated OE7, where EO is ethylene oxide monomer and EE is ethylethylene monomer), has been shown to self-assemble into membranes that are hyper-thick compared to any natural lipid membrane and are also an order of magnitude or more tougher, and thus, show greater mechanical stability. (Discher B M, Won Y-Y, Ege D S, Lee J C-M, Bates F S, Discher D E, Hammer D A., *Science,* 1999; 284:1143-1146.) Augmented chemical stability due to their polyethylene-oxide (PEO) head groups confers biocompatibility, structural integrity in plasma, and "stealth"-like character resulting in long in vivo circulation times. (P. J. Photos, L. Bacakova, B. Discher, F. S. Bates, D. E. Discher, *Journal of Controlled Release* Jul. 31, 2003; 90, 323-334.) A novel PEO-PBD diblock, $EO_{26}$-$BD_{46}$ (designated OB2, where EO is ethylene oxide monomer and DB is butadiene monomer), has also been shown to be capable of making vesicles. Both OE7 and OB2 have mean molecular weights in excess of several kDa—much larger than any natural membrane-forming amphiphile. Another diblock capable of making vesicles is PEO-PCL, $PEO_{45}$-$PCL_{105}$ (designated OL1 where PCL is poly(ε-caprolactone)).

Dependent upon the structure of their component copolymer blocks, polymersome membranes can be significantly thicker (~9-22 nm) than those of liposomes comprised of natural phospholipids (3-4 nm). (See H. Bermudez, A. K. Brannan, D. A. Hammer, F. S. Bates, D. E. Discher, *Macromolecules* 35, Oct. 8, 2002; 8203-8208.) These thick membranes of synthetic vesicles not only exhibit enormous mechanical stability, but also provide sufficient size to solubilize and stably incorporate large hydrophobic compounds. Depending on the size of the vesicles composite amphiphilic building blocks, hydrophobic compounds of any size and molecular weight can be easily incorporated in polymersome membranes. Large (greater than 2 nm in size is 1 kD in MW) hydrophobic compounds (like porphyrin dimers, trimers, tetramers, pentamers) are unable to be accommodated in natural sized membranes composed of phospholipids.

In one preferred embodiment, the radiofrequency absorptive moiety in the hydrophobic membranes of the polymersomes is meso-to-meso ethyne-bridged bis[(porphinato)zinc] ($PZn_2$) chromophore. $PZn_2$ spans a peak emission wavelength of 723 nm. In other embodiments, the radiofrequency absorptive moiety can be $PZn_1$, $PZn_3$, $PZn_4$ or $PZn_5$. Any porphyrin would be sufficient for use in some embodiments of this invention. The substituents on PZn multimers can be varied as desired, and the linkage chains between them as well. Preferred embodiments have a radiofrequency absorptive moiety with a large extinction coefficient and a low quantum yield because molecules with a low quantum yield release the most heat after absorbing energy. The thicker the polymer wall is in the polymer vesicle, the longer the chain of PZn that can be incorporated in the membrane, leading to increased heat release. Increased heat release results in increased budding of the polymer vesicle. Hydrophilic dyes may be functionalized with hydrophobic groups so as to make them hydrophobic and therefore capable of associating with the polymer vesicle membrane.

In preferred illustrative embodiments, the protein in the lumen of the vesicle and associated with the inner leaflet of the membrane is either horse spleen ferritin (HSF) or iron-free apoferritin (HSAF). Ferritins are a ubiquitous family of large iron-storage proteins (MW≈440 kDa) that can sequester up to 4500 iron atoms as a hydrous ferric oxide mineral core and can serve as a magnetic resonance imaging contrast agent. (Harrison, P. M.; Arosio, P. BBA-*BIOENERGETICS*, 1996, 1275, 161-203, Theil, E. C. *Journal of Nutrition*, 2003, 133, 1549S-1553S, Chasteen, N. D.; Harrison, P. M. *J STRUCT BIOL*, 1999, 126, 182-194.) Twenty-four 4-helix bundle subunits form a 12-nm sphere with an 8-nm cavity that remains stable over a wide range of pH and temperature and has been demonstrated to sequester many organic small molecules and other metals. (Jeong, G. H.; Yamazaki, A.; Suzuki, S.; Yoshimura, H.; Kobayashi, Y.; Homma, Y. *J. Am. Chem. Soc.*, 2005, 127, 8238-8239, Webb, B.; Frame, J.; Zhao, Z.; Lee, M. L.; Watt, G. D. *ARCH BIOCHEM BIOPHYS*, 1994, 309, 178-183, Simsek, E.; Kilic, M. A. J *MAGN MAGN MATER*, 2005, 293, 509-513.) In some embodiments the HSF or HSAF are labeled with Cy3 fluorophore. Cy3 labels surface lysines of a protein. In other embodiments, the HSF or HSAF are labeled with BODIPY-FL fluorophore. BODIPY-FL labels surface cysteines of a protein. In some embodiments, the protein in the lumen of the vesicle and associated with the inner leaflet of the membrane is bovine serum albumin (BSA) or myoglobin (Mb). In some embodiments, the BSA or Mb were labeled with Cy3 fluorophore. In other embodiments, the BSA or Mb are labeled with BODIPY-FL fluorophore.

In one aspect of the invention, the polymer vesicle further comprises at least one targeting moiety on the membrane external to the lumen of the vesicle. By utilizing a targeting moiety that can direct the polymersome to a particular cell type, tissue, or location, the polymersomes of the invention become more effective, discriminatory and selective. The term "targeting moiety" is defined herein as a functional group which serves to target or direct the polymersome to a particular location, cell type, organ, diseased tissue, or other targeted cell sites. In some preferred embodiments, the targeting moiety is an antibody, cell surface receptor ligand, hormone, lipid, sugar, dextran, alcohol, bile acid, fatty acid, amino acid, peptide or nucleic acid. The targeting moiety can be attached to the amphiphilic block copolymer using linking chemistry techniques known to those skilled in the art. In some embodiments, the targeting moiety is covalently bound to the block copolymer. In some embodiments, the targeting moiety is bound to the hydrophilic polymer. In other embodiments, the targeting moiety is associated with the polymersome by non-covalent bonding interactions such as ionic or by van der Waals forces. In certain preferred embodiments, the targeting moiety is comprises an antibody, antibody fragment, or a receptor binding site or substance. In yet other embodiments, the receptor binding site or substance comprises a receptor-specific peptide, carbohydrate, or protein. Techniques for attaching biological molecules to a wide variety of chemical functionalities have been catalogued by Hermanson, et al., *Immobilized Affinity Ligand Techniques*, New York, N.Y.: Academic Press, Inc. (1992).

The targeting moiety is optionally attached to the polymersome by a linking group. Suitable linking groups are those that provide a desired degree of flexibility without any detrimental effects to the polymersome/imaging agent system. In a preferred embodiment, avidin is attached to the outer polymer membrane. The avidin binds biotinylated antibodies to the outside of the polymer vesicle. Avidin may thus be employed to bind any biotinylated targeting moiety to the polymer vesicle. (Hammer et al., *Faraday Discussions*, 2008, 139, 129.)

In some embodiments, the invention concerns a composition for intracorporeal administration comprising polymer vesicles wherein the polymer vesicles comprise an encapsulating polymer membrane, and a radiofrequency absorptive moiety either forming part of the membrane or attached or conjugated to the membrane external to the lumen of the vesicle said vesicle further comprising protein in the lumen of the vesicle and associated with the inner leaflet of the membrane and therapeutic or diagnostic cargo in the lumen of the vesicle. The polymer vesicles may be formulated differently depending on the route of administration chosen. They may be in lyophilized form, liquid form, frozen form or powder form. In some embodiments, the polymer vesicles may be formulated in aqueous solutions for injection. In other embodiments, topical or transdermal formulations may include stabilizers and/or oxidants. In particular embodiments, the polymer vesicles may be formulated for intracorporal administration by combining them with pharmaceutical carriers and diluents known in the art. Suitable pharmaceutical carriers and diluents are described in the most recent edition of Remington's Pharmaceutical Sciences, A. Osol, a standard reference text in this field which is incorporated by reference in its entirety. Compositions may be administered by an appropriate route such as, for example, by intravenous, oral, intranasal, cutaneous, anal, gastrointestinal, intraocular and intratumoral administration.

Therapeutic or diagnostic cargo in the vesicle may include pharmaceutical compositions, chemotherapeutic agents, radiopharmaceuticals, dyes, magnetic imaging contrast agents, proteins, organic molecules, inorganic molecules and antigens. In one aspect of the invention, vesicles loaded with antigens may serve to immunize a patient against the antigen.

In one aspect of the invention, the composition for intracorporeal administration comprises polymer vesicles that further comprise at least one targeting moiety on the membrane external to the lumen of the vesicle. Possible targeting moieties have been described supra.

In some embodiments, the invention concerns a method for releasing a therapeutic or diagnostic material at a preselected site inside the body of a subject comprising the steps of: (a) administering to the subject a composition comprising polymer vesicles; (b) wherein said polymer vesicles comprise an encapsulating polymer membrane, and contained within the polymer membrane, a radiofrequency absorptive moiety and internal to the polymersome a protein constraining the inner leaflet of the membrane, further comprising a therapeutic cargo internal to the polymersome, and (c) exposing said selected site with electromagnetic radiation effective for releasing said therapeutic or diagnostic agent from the vesicles.

Upon irradiation by electromagnetic radiation, the radiofrequency absorptive moiety in the membrane of the polymer vesicles absorb the energy, are thereby heated, and then rupture. In a preferred embodiment, the radiofrequency absorptive moiety is $PZn_2$. Incorporation of PZn2 into the vesicle's hydrophobic membrane imparts sensitivity to focused light of UV to near-IR wavelengths. In preferred embodiments, the protein constraining the inner leaflet of the membrane is ferritin or apoferritin. In other embodiments, the protein may be BSA or Mb. As discussed supra, the protein may be labeled or unlabeled with a fluorescent dye.

The electromagnetic radiation may comprise a laser beam, or light from fluorescent lamps, tungsten-halogen lamps, light emitting diodes, high intensity sources, broad spectrum and non-chromatic sources, and microwave. Cutoff filters for selectively passing all wavelengths above or below a selected wavelength may be employed. The light source may be a high or low intensity source. The emitted light can be continuous wave (CW) light, time-resolved (TR) light, or both CW and TR light. Non-continuous illumination techniques may also be employed.

In a preferred embodiment, the electromagnetic radiation was a laser beam. In another preferred embodiment, the electromagnetic radiation was light from a fluorescent lamp.

In one aspect of the invention, the method for releasing a therapeutic material at a preselected site inside the body of a subject comprises polymer vesicles that further comprise at least one targeting moiety on the membrane external to the lumen of the vesicle. Possible targeting moieties have been described supra.

Provided are polymer vesicles for intracorporeal administration comprising an encapsulating polymer membrane, and a radiofrequency absorptive moiety either forming part of the membrane or attached or conjugated to the membrane, preferably external to the lumen of the vesicle; said vesicle further comprising polysaccharide in the lumen of the vesicle and associated with the inner leaflet of the membrane; as well as a therapeutic or diagnostic cargo in the lumen of the vesicle.

In some aspects, the polysaccharide in the lumen of the vesicle and associated with the inner leaflet of the membrane of the vesicle is dextran, pectin, chitosan, pullulan, carboxymethylpullulan, dextrin, curdlan, levan, schizophyllan, or combinations thereof.

Provided are compositions for intracorporeal administration comprising polymer vesicles wherein the polymer vesicles comprise an encapsulating polymer membrane, and a radiofrequency absorptive moiety either forming part of the membrane or attached or conjugated to the membrane external to the lumen of the vesicle; said vesicle further comprising polysaccharide in the lumen of the vesicle and associated with the inner leaflet of the membrane, and therapeutic or diagnostic cargo in the lumen of the vesicle in a pharmaceutically acceptable carrier or diluent. In some compositions for intracorporeal administration, the polymer vesicles further comprise at least one targeting moiety on the membrane external to the lumen.

Provided are methods for releasing a therapeutic or diagnostic material at a preselected site inside the body of a subject. The subject is first administered a composition comprising vesicles; wherein said vesicles comprise an encapsulating polymer membrane. Contained within the polymer membrane is a radiofrequency absorptive moiety, and internal to the polymersome there is a protein constraining the inner leaflet of the membrane. The vesicles further comprise a cargo internal to the polymersome. The selected site is then exposed with electromagnetic radiation effective for releasing said therapeutic or diagnostic agent from the vesicles.

The present invention is further defined in the following Examples, in which all parts and percentages are by weight and degrees are Celsius, unless otherwise stated. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various usages and conditions.

EXAMPLES

Example 1

Polymersome Assembly. Thin films of polymer were created on roughened Teflon surfaces by depositing 200 µL of a 1 mM solution of OB29 with or without porphyrin dye at a 5:1 molar ratio (polymer:dye) in methylene chloride. Films were dried in a vacuum oven for 12 h and then hydrated with 1 or 2 mL of a 290 mOsm sucrose+PBS buffer with or without protein at 65° C. for 24 h. Vesicle solutions were vortexed after heating. Vesicles are depicted in FIG. 1.

Example 2

Vesicle Separation. Vesicles were separated from free protein by diluting 500 µL polymer vesicle solution in 9.5 mL PBS+1% BSA. This solution was then placed on a 2 mL cushion of sucrose buffer+density gradient medium in a centrifuge tube. The tube was spun at 20,000 rpm for 1 h, and the resulting band of 500-1000 µL concentrated solution of vesicles was removed. Samples were then dialyzed into 290 mOsm PBS within 20,000 Da MWCO dialysis cassettes for 12 h at 4° C.

Example 3

Chemical labeling of HSF, HSAF, BSA and Mb. The concentration of HSAF, BSA, or Mb was determined by UV-Vis spectroscopy ($\epsilon_{280}$=480,000 $M^{-1}cm^{-1}$ for HSAF,[2] $\epsilon_{280=44,300}$ $M^{-1}cm^{-1}$ for BSA, and $\epsilon_{280}$=15,400 $M^{-1}cm^{-1}$ for Mb). BSA required several FPLC size-exclusion purification steps to eliminate protein aggregates and fragments. The concentration of HSF was determined by Bradford assay. The Cy3 dye was used to label surface lysines on the protein, whereas BODIPY-FL labeled surface cysteines. The protein labeling protocols provided by the manufacturers were followed for both Cy3 and BODIPY-FL conjugations, with the following modifications. For the Cy3 labeling: i) 10 mg/mL protein in 290 mOsm PBS was used, ii) the conjugation reaction was carried out for 2-3 h, and iii) the labeled protein was separated from free dye with 290 mOsm sucrose+PBS buffer. For the BODIPY-FL labeling: i) 500-fold molar excess (20-fold per ferritin subunit) of TCEP was used, ii) 400-fold molar excess (17-fold per ferritin subunit) of dye was used, and iii) the labeled protein was separated from free dye with 290 mOsm sucrose+PBS buffer. Absorbance measurements were made by UV-Vis spectroscopy with an Agilent 8453 spectrophotometer with temperature controller and magnetic stirrer (Agilent 89090A), using a quartz cuvette with 1-cm pathlength. The maximum absorbance of BODIPY-FL and Cy3 are at 502 nm and 550 nm, with molar extinction coefficients of 76,000 $M^{-1}cm^{-1}$ and 150,000 $M^{-1}cm^{-1}$, respectively. Labeling efficiency for HSAF was quantified as described in the manufacturer protocols.

Example 4

Confocal microscopy of polymer vesicles incorporating HSAF and $PZn_2$ to show budding. Fluorescence scanning confocal microscope images of polymer vesicles incorporating either labeled or unlabeled HSAF and $PZn_2$ were obtained using a Radiance 2000 Multi-Photon Confocal System (Bio-Rad laboratories, Hercules, Calif.) equipped with a 650 nm long-pass emission filter. CLSM imaging of polymersomes loaded with both ferritin and $PZn_2$ under laser illumination at various wavelengths (488 nm, 543 nm, 633 nm) caused many vesicles to undergo significant morphological changes. $PZn_2$ absorbs strongly at these wavelengths. (Duncan, T. V.; Susumu, K.; Sinks, L. E.; Therien, M. J. *J. Am. Chem. Soc.* 2006, 128, 9000-9001.) Similar results were seen during imaging by widefield fluorescence microscopy using a mercury arc lamp. These changes varied from the formation of new bends or "arms" to the budding of smaller vesicles and the complete destruction of the polymersome itself.

Figure 2:
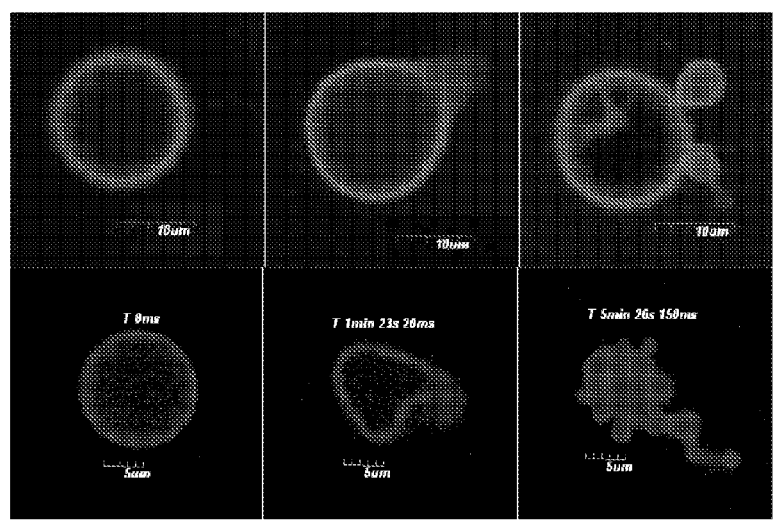
FIG. 2 shows overlay images of $PZn_2$ encapsulated in the membrane bilayer (dark gray) and BODIPY-FL (light gray)-labeled apoferritin in the vesicle; each vesicle was scanned continuously. (A) BODIPY-FL-labeled HSAF (3 mg/mL)+$PZn_2$ (dark gray) vesicle. Vesicle imaged using two lasers (488 nm, 543 nm). The three images are stills (proceeding in time left to right) over a period of approximately 5 min. (B) unlabeled HSAF (1.5 mg/mL)+$PZn_2$ (dark gray) vesicle. Vesicle imaged using three lasers (488 nm, 543 nm, 633 nm). Images are stills. Final image is at a lower plane than other images, as the degraded structure was not in the same plane as the original vesicle. The number of vesicles that change shape within a population increases as the ferritin concentration in the hydration buffer increases.

FIG. 2 demonstrates fluorescence emission from polymer vesicles incorporating BODIPY-FL-labeled HSAF (3 mg/mL) and $PZn_2$, as well as from polymer vesicles incorporating unlabeled HSAF (1.5 mg/mL) and $PZn_2$.

Example 5

Figure 3:
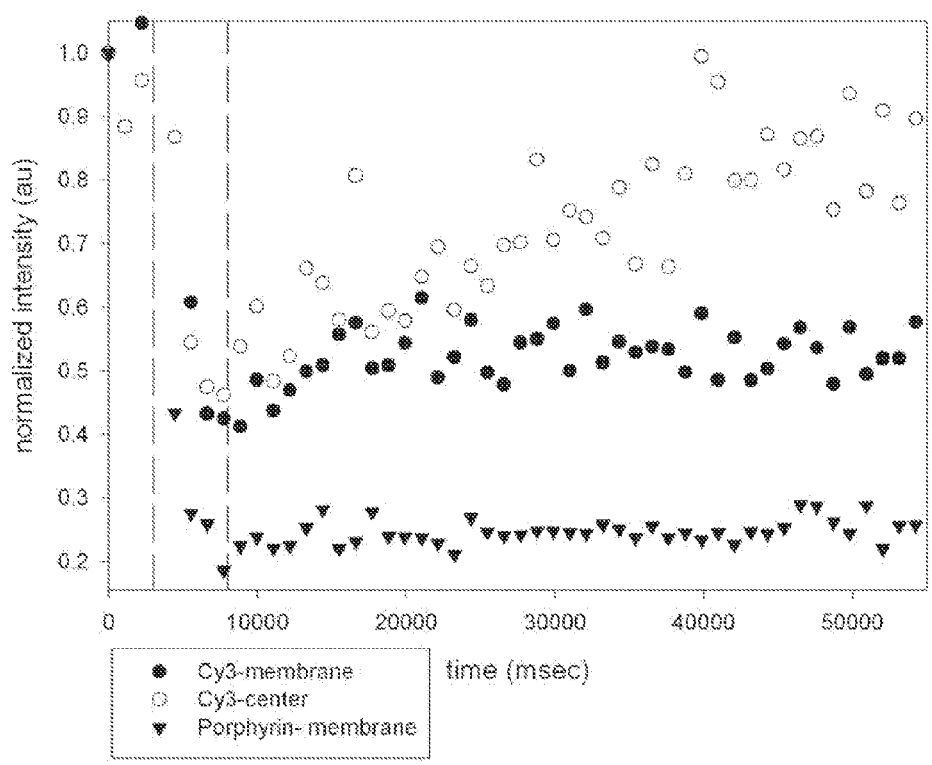
FIG. 3 illustrates fluorescence recovery after photobleaching (FRAP) experiments on vesicles containing 1.5 mg/mL Cy3-labeled HSAF show no fluorescent recovery of Cy3 at membrane surface, but Cy3 intensity in the vesicle interior almost completely recovers after photobleaching. $PZn_2$-based emission intensity at the membrane did not recover and is plotted as a reference. Photobleaching occurred during the time period indicated by dashed vertical lines.

Fluorescence Recovery After Photobleaching (FRAP). To measure $PZn_2$ and ferritin mobility in the polymersome, fluorescence recovery after photobleaching (FRAP) experiments were performed. Experiments with OB29 vesicles containing only $PZn_2$ confirmed that the motion of dye molecules within the membrane was restricted, with no $PZn_2$ fluorescence recovery observed 1 min after photobleaching (FIG. 3). FRAP experiments performed on vesicles containing both fluorescently labeled HSAF and $PZn_2$ showed similarly restricted diffusion of $PZn_2$ at the membrane. In all FRAP studies, OB29 polymersomes containing HSF behaved similarly to vesicles containing HSAF. FRAP experiments were carried out on an Olympus Fluoview FV1000 confocal microscope (Center Valley, Pa.), equipped with a UPLFLN 40× oil objective lens. The FV1000 comes equipped with a SIM scanner system, allowing for confocal imaging and laser stimulation to be carried out independently and virtually simultaneously. A 351 nm laser at 90% power was used to bleach small regions of polymersomes for 10 seconds. The fluorescence intensities of the regions were tracked before, during, and after bleaching, using lasers of appropriate wavelengths (488 nm for BODIPY-FL, 543 nm for Cy3, and 633 nm for $PZn_2$) scanning at 2 μs/pixel. The measured intensities were plotted against time to generate fluorescence recovery curves. For polymersomes containing $PZn_2$ and the more dispersed Cy3-labeled HSAF, FRAP was measured at two locations: the vesicle membrane and the aqueous core. Significant recovery of Cy3 fluorescence was observed in the aqueous core. However, no significant Cy3 fluorescence recovery was observed upon bleaching at the membrane, indicating very slow exchange between HSAF molecules both in the membrane, and between the aqueous core and the membrane. Membrane photobleaching of samples containing BODIPY-FL-labeled ferritin showed a similar lack of fluorescence recovery. CLSM images of vesicles loaded with BODIPY-FL-labeled Mb or BSA showed that Mb associated predominantly with the polymer membrane, whereas BSA was present throughout the aqueous core. The results of FRAP experiments on these vesicles were similar to those done with HSAF and HSF vesicles.

In conclusion, without wishing to be bound to one theory of operation, Ferritin associates with the polymer vesicle membrane. FRAP experiments reveal minimal diffusion of ferritin associated with the membrane and unhindered diffusion of ferritin in the aqueous core. The negative charge on the Cy3 dye provides the driving force to allow some protein to remain in the aqueous core. The chelating iron in ferritin does not change the interaction of protein with the vesicle membrane. Laser light and epifluorescence both induce shape change and/or budding in some vesicles, regardless of light wavelength or fluorophore requirement for light-triggered shape changes.

Example 6

HSAF Release. Release of small molecules from HSAF-$PZn_2$ vesicles during light-induced budding was demonstrated through the encapsulation of biocytin and exposure of samples to fluorescent light. Two experiments were performed, one immediately after vesicle hydration and the other after 7 days storage at 4° C. These experiments indicated that biocytin remains in the vesicle interior during storage and that exposure to fluorescent light activates release Four OB29 films were deposited on roughened Teflon squares using the procedure described previously; three of these films contained $PZn_2$ porphyrin dimer at the 5:1 molar ratio (polymer:dye) used in all other experiments. Films were dried in a vacuum oven for multiple days. After drying, the films were hydrated with the same sucrose+PBS buffer used in previous experiments to make 4 samples: OB29+2 mL buffer containing HSAF at 10 mg/mL, OB29+$PZn_2$+2 mL buffer, OB29+$PZn_2$+2 mL buffer containing HSAF at 10 mg/ml, OB29+$PZn_2$+1 mL buffer containing HSAF at 10 mg/mL. 200 μL of PBS containing biocytin at 5 mg/mL were added to each sample during hydration. Samples were placed in a 65° C. oven for 24 hours and vortexed for 1 min while hot after heating. Free HSAF was separated from samples by centrifugation. 500 μL of each sample was then diluted in 9.5 mL of PBS containing 1% BSA by weight. A cushion of 80% sucrose buffer/20% optiprep buffer (by volume) was placed at the bottom of each diluted sample. Tubes were spun at 20,000 rpm for 60 min at 4° C., and approximately 1.5 mL concentrated polymersomes were removed from the interface of the two buffers. Samples were then placed in 10,000 Da MWCO dialysis cassettes and dialyzed in 4 L PBS. Buffer was changed 24 hours into dialysis. The volumes changed during dialysis so that approximately 2-2.5 mL was removed from each dialysis cassette. Samples were analyzed using a UV/Vis spectrometer to evaluate relative concentrations based on the absorbance of the $PZn_2$. The 4 samples were then put in glass cuvettes with screwtop caps and stirbars. These samples were placed on a stirplate (which agitated the samples very slowly) in front of a mercury arc lamp for 4 hours. After 4 hours, samples were removed from in front of the arc lamp and analyzed again with the UV/Vis spectrometer. 1.5 mL of each sample was then placed in a 5000 Da MWCO AMICON centrifuge filter tube and spun at 2500×g for 10 min so that each tube contained 250 μL concentrated sample and approximately 1.25 mL filtrate. 100 μL of unseparated vesicles, concentrated sample, and filtrate from each of the 4 samples was added to wells of a black 96-well untreated plate.

Figure 4:
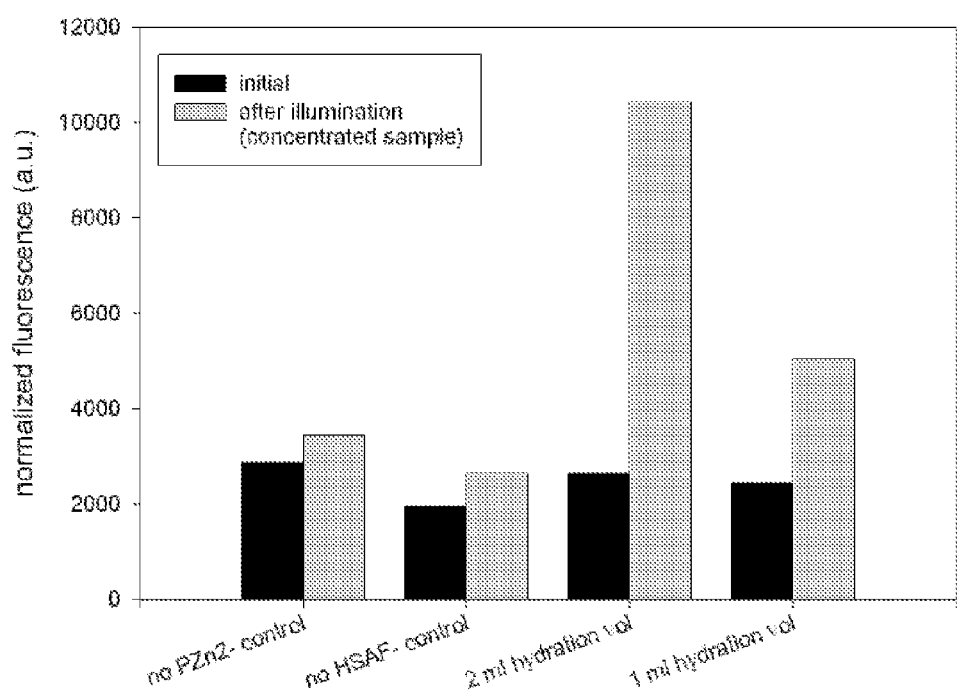
FIG. 4 illustrates biocytin release from the vesicles. Biocytin reporter fluorescence divided by relative concentrations of samples shows significant increase of biocytin present in positive samples compared to controls. Initial data point shows that all samples have similar low levels of biocytin in solution initially. Increased fluorescence between initial and final data points show that biocytin in not released from positive samples during 7 day storage.

100 μL of 2× green reagent (biotin quantitation, FluoReporter biotin quantitation assay kit for biotinylated proteins, Invitrogen, Carlsbad, Calif.) was added to each well. The solution was allowed to react for 5 minutes, protected for light. The fluorescence was read at 485/550 nm (excitation/emission) using a fluorometer. The fluorescence values reported in FIG. 4 are based on the average of 25 flashes. The excitation bandwidth was 9 nm, the emission bandwidth was 20 nm, and the integration time was 20 μs.

Example 7

Figure 5:
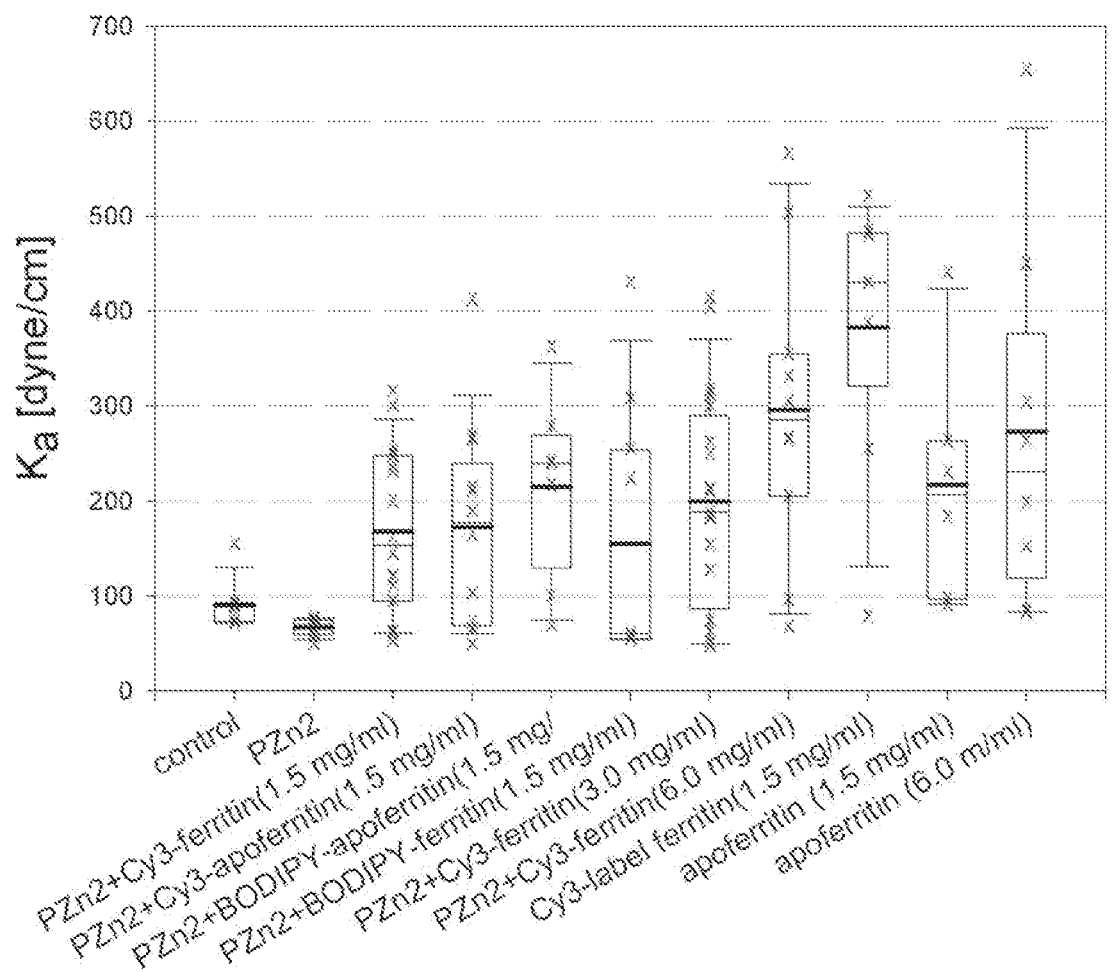
FIG. 5 illustrates data collected during micropipette aspiration experiments. Ferritin encapsulation increases the average static modulus of a population of vesicles, but it does not uniformly affect each vesicle within the population. DD indicates that porphyrin su-peg dimer ($PZn_2$) is contained in the membrane bilayer.
Figure 6:
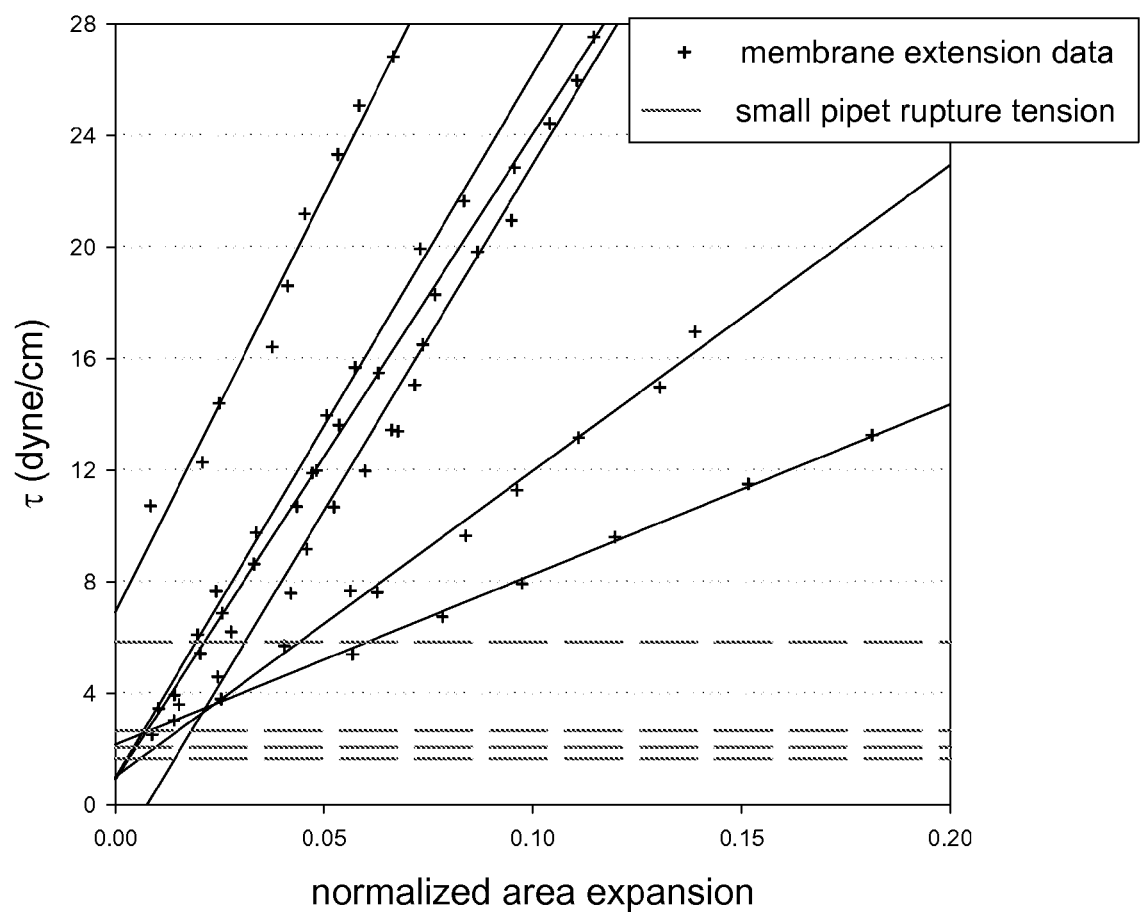
FIG. 6 illustrates micropipette aspiration data for 1.5 mg/mL Cy3-labeled ferritin+$PZn_2$ samples. The dashed horizontal lines indicate tensions at which vesicles ruptured when aspirated with small pipettes (<5 μm). The (+)-signs indicated tensions exerted on vesicles without rupture using larger pipettes (~9 μm). Ferritin encapsulation results in vesicle rupture at low tension when aspirated with small pipettes (<5 μm ID). This phenomenon is observed with both uni-lamellar and multi-lamellar vesicles.
Figure 7:
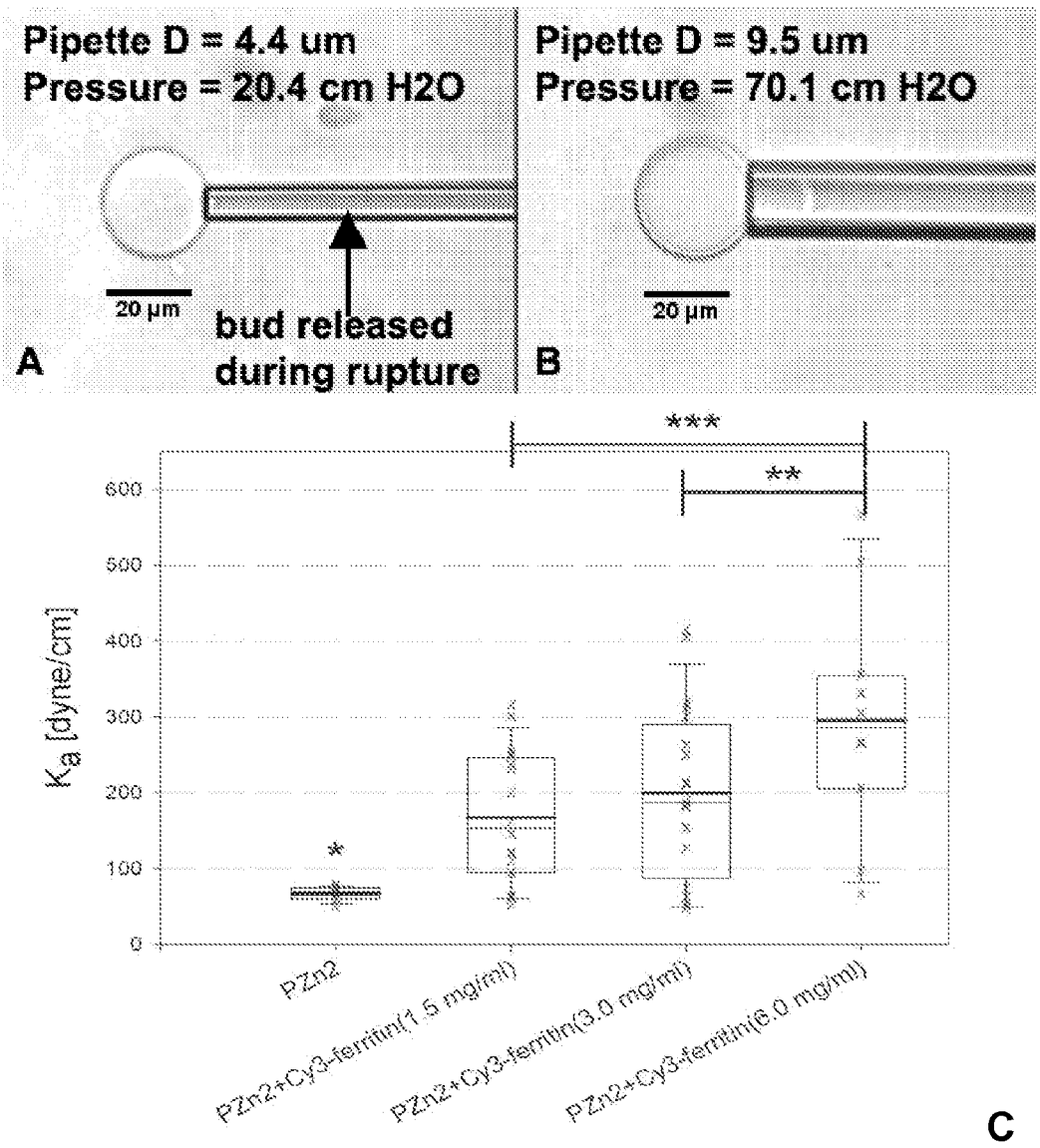
FIG. 7 illustrates images of micropipette aspiration experiments performed on vesicles containing 1.5 mg/mL Cy3-labeled ferritin+$PZn_2$. Experiments performed with small pipettes (ID<5 μm) result in rupture at low tensions (A) while vesicles remain intact at high tensions in experiments performed with larger pipettes (B). These results suggest that the bending rigidity of vesicles that incorporate ferritin is significantly decreased compared to control vesicles. (C) Micropipette aspiration results for vesicles incorporating $PZn_2$ and Cy3-labeled ferritin at various hydration concentrations. A box and whiskers plot is superimposed over each data set. The mean (bold line) and median (thin line) are indicated within the boxes. The box indicates the middle 50% of the range, and the whiskers indicate 95% and 5% of the range. A 1-sided t-test was used to determine confidence that the average elastic modulus for each sample was different from other samples; *=>99.999% confidence compared to each ferritin-incorporating sample, =95% confidence, *=98% confidence. Neither fluorescent label identity nor the presence of iron changes the effect of ferritin on membrane strength. Increased ferritin concentration results in an increase in average elastic modulus and range of moduli for a population of vesicles. All vesicles contain $PZn_2$, referred to here also as porphyrin su-peg dimer (DD) in membrane bilayer.

Micropipette Aspiration. Micropipettes made of borosilicate glass tubing (Friedrich and Dimmock, Milville, N.J.) were prepared using a needle/pipette puller (Model 720, David Kopf Instruments, Tujunga, Calif.) and microforged using a glass bead to give the tip a smooth and flat edge. The inner diameter of the pipettes ranged from 4.7 to 10.4 μm, and they were measured using microscopy and computer imaging software. Pipettes were filled with 290-295 mOsm PBS, then the surfaces were blocked with DPBS+1% BSA for 2 min. The pipettes were then connected to an aspiration station mounted on the side of a Zeiss inverted microscope, equipped with a manometer, Validyne pressure transducer (models DP 15-32, and DP 103-14, Validyne Engineering Corp., Northridge, Calif.), digital pressure read-outs, micromanipulators (model WR-6, Narishige, Tokyo, Japan), and Melles-Griot millimanipulators (course x, y, z control). Suction pressure was applied via a syringe attached to the manometer. Vesicle-containing solutions in sucrose/PBS buffer (290-295 mOsm) were either diluted with an equal volume of 290-295 mOsm PBS or dialyzed overnight into PBS. Pipettes were used to select single vesicles. Pressure was increased stepwise in 5 cmH$_2$O increments, and the membrane was allowed one min after each pressure change to equilibrate. Experiments were imaged using DIC optics with a 40× objective and a Cohu black-and-white CCD camera (Cohu, Inc., San Diego, Calif.). ImageJ software was used to measure membrane extensions and vesicle diameters. Calculations of tension and area extension were performed using force balances discussed extensively by Evans and coworkers. (E. A. Evans, *Biophys. J.*, 1973, 13, 941.) The results are illustrated in FIGS. 5, 6 and 7.

In conclusion, without wishing to be bound to one theory of operation, the range of triggers and lack of fluorophore requirement for light-triggered shape change suggests local heating is responsible for vesicle shape changes. Encapsulation of ferritin increases the average elastic modulus of polymersome populations but the increase in strength is not homogeneous. Increased ferritin concentration in aqueous solvent increases the population average elastic modulus but not the minimum elastic modulus. Decreased rupture tension in small diameter pipettes suggests ferritin interactions decrease membrane bending modulus. Distribution within measurements suggests non-uniform encapsulation of ferritin within vesicles.

Example 8

Flow Cytometry. Polymer films were prepared and HSAF was labeled with BODIPY-FL as described. Films were hydrated with 1 mL sucrose+PBS buffer containing 0.5, 1.5, 3.0, 6.0, 10.0, or 15.0 mg/mL of HSAF. Samples were separated by ultracentrifugation as previously described and dialyzed overnight in PBS using 20 kDa MWCO Slide-A-Lyzer dialysis cassettes. A FACSCalibur flow cytometer (BD Biosciences, Franklin Lakes, N.J.) was used to analyze samples. BODIPY-FL intensity was measured using the FL1 channel, and PZn$_2$ intensity was measured using the FL3 channel. Compensation was achieved using single positive fluorescent samples, and 25,000 events within a gate on vesicles larger than 1 μm diameter were counted for each experiment. Thresholding was set to zero, and all events were recorded during experimentation. Samples were protected from light during all steps of preparation. Analysis of flow cytometry data was performed using CellQuest/FlowJo software (BD Biosciences, Franklin Lakes, N.J./Tree Star, Inc, Ashland, Oreg.).

Figure 8C:
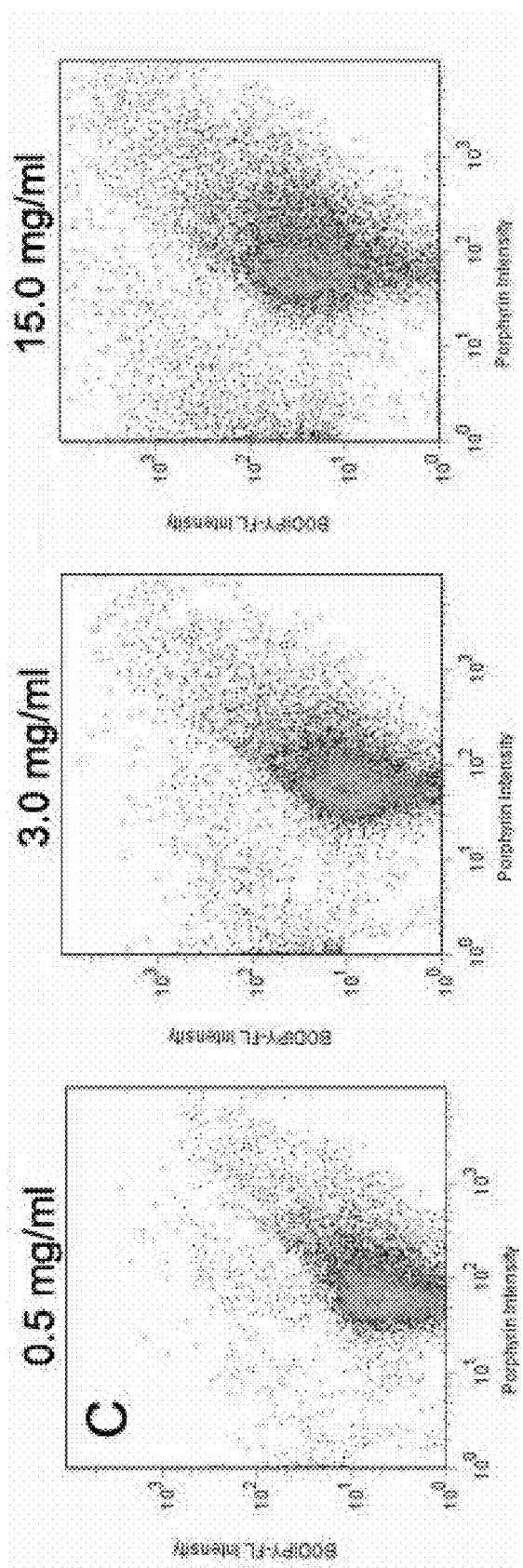
FIG. 8 illustrates forward scatter vs. side scatter dot plot for three populations of vesicles (A). Dynamic light scattering (DLS) plot shows size distribution for these populations (B). The blue, square shaped region on the dot plot is excluded from calculations because it is impossible to distinguish sub-500 nm vesicles from free protein, amorphous polymer aggregates, and other debris. Three dot plots of porphyrin intensity (membrane surface area) versus BODIPY-FL fluorescence (corresponding to ferritin concentration) show that the average concentration of ferritin encapsulated within a population of vesicles increases with increasing concentration of ferritin in the hydration solution. The scatter also increases, which indicates a heterogeneous distribution of ferritin in a sample of similar size vesicles (C). A histogram of BODIPY-FL intensities for the different samples supports this finding, and the lack of a peak shift from the 10.0 mg/mL to 15.0 mg/mL sample indicates that there may be a limit in the amount of ferritin that a population of vesicles can incorporate (D).
Figure 8D:
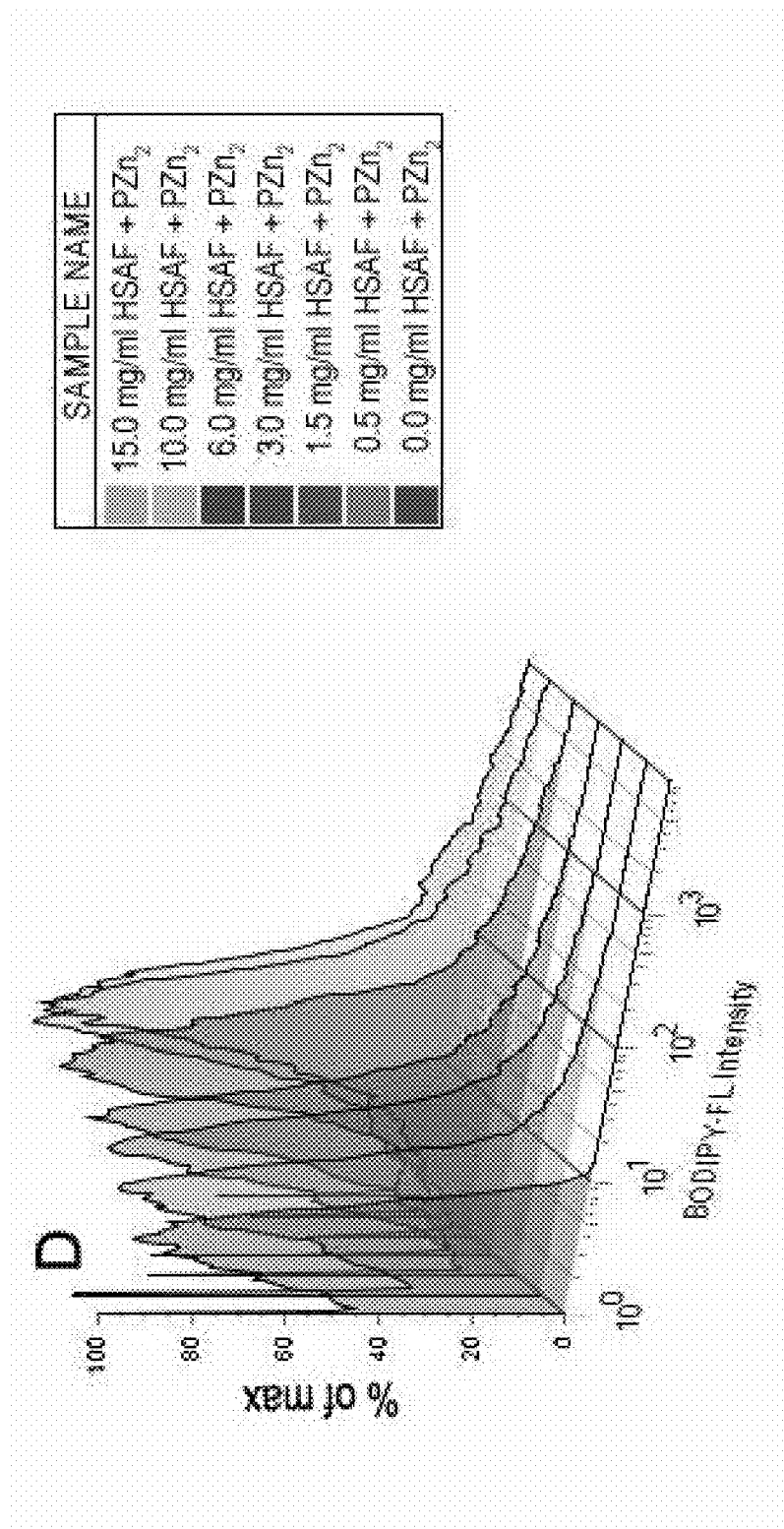
Figure 9:
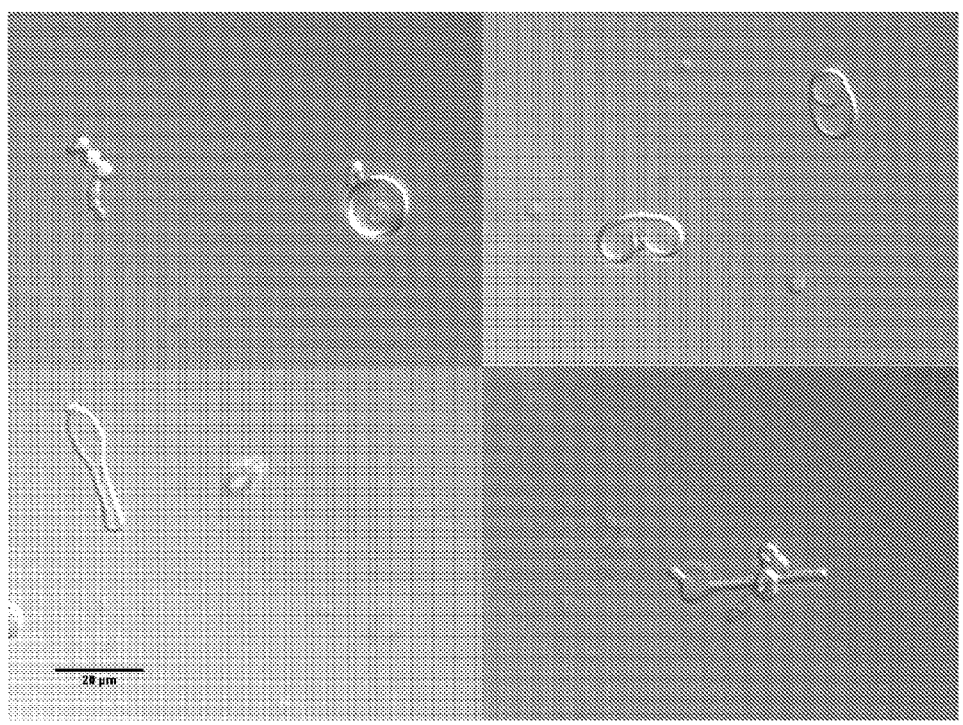
FIG. 9 illustrates ferritin-encapsulating polymer vesicles forming in a variety of asymmetric shapes. All vesicles are loaded suspended in 290 mOsm solutions osmotically matched to the solutions within the aqueous core.
Figure 10:
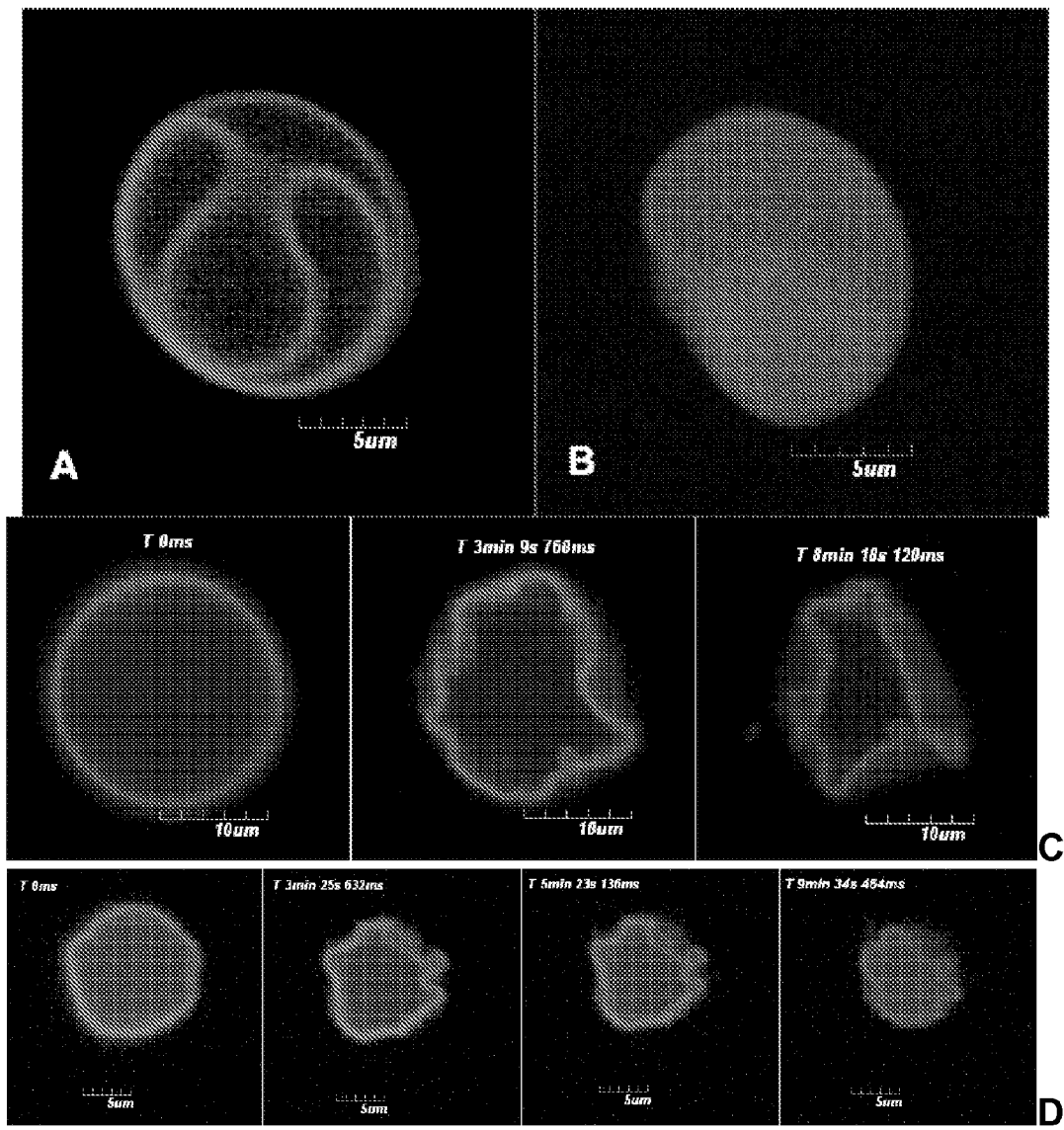
FIG. 10 illustrates overlay images of $PZn_2$ encapsulated in the membrane bilayer (light gray) and either BODIPY-FL (diffuse dark gray in A)-labeled (apo)ferritin or Cy3 (diffuse bright gray in B)-labeled (apo)ferritin in the vesicle. (A) BODIPY-FL-labeled ferritin (1.5 mg/mL) localizes almost completely at the membrane. (B) Cy3-labeled ferritin (1.5 mg/mL) is diffuse throughout the aqueous core. (C) unlabeled HSAF (9.9 mg/mL)+$PZn_2$ (light gray) vesicle. This vesicle was imaged using three lasers (488 nm, 543 nm, 633 nm) on the CLSM. The three images are stills (proceeding in time from left to right, as indicated by the timestamp) during which the vesicles were continuously scanned. The light gray denotes $PZn_2$ encapsulated in the membrane bilayer. (D) myoglobin (10 mg/mL)+$PZn_2$ (light gray) vesicle. This vesicle was imaged using three lasers (488 nm, 543 nm, 633 nm) on the CLSM. The three images are stills (proceeding in time from left to right, as indicated by the timestamp).
Figure 11:
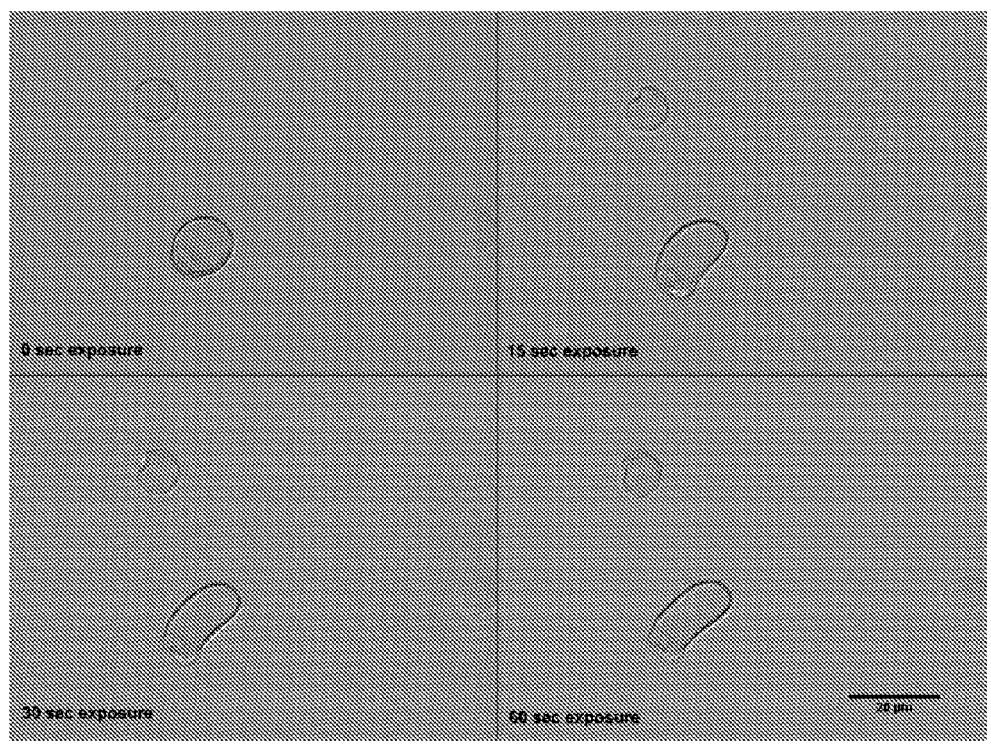
FIG. 11 illustrates 9.9 mg/mL unlabeled HSAF+$PZn_2$-labeled vesicle. These images were obtained by confocal laser scanning microscopy (CLSM) using DIC optics. The timestamp refers to total exposure of these vesicles to a mercury arc-lamp. Both vesicles in these images deform during the periods in which they are exposed to light from the arc lamp.
Figure 12:
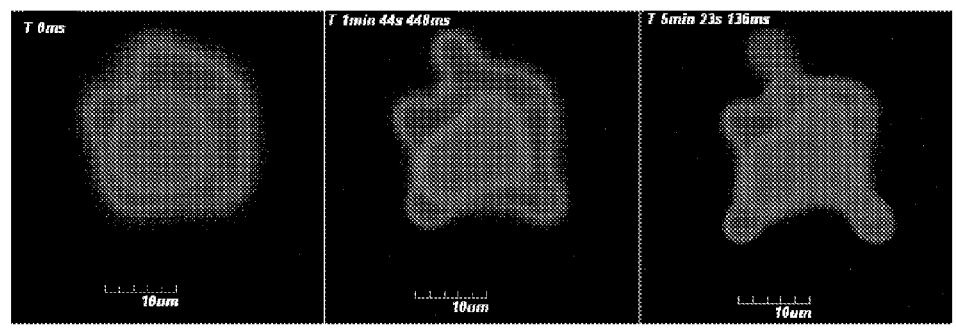
FIG. 12 illustrates 9.9 mg/mL BSA+$PZn_2$-labeled vesicle. This vesicle was imaged using three lasers (488 nm, 543 nm, 633 nm) on the CLSM. The three images are stills (proceeding in time from left to right, as indicated by the timestamp).
Figure 13:
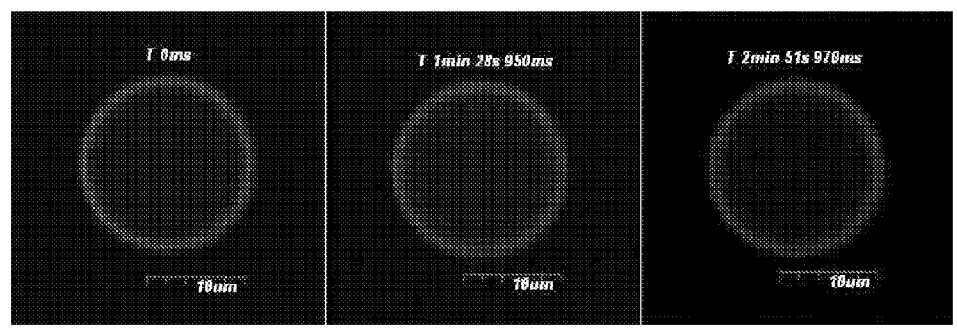
FIG. 13 illustrates 1.5 mg/mL unlabeled apoferritin+Nile Red-labeled vesicle. This vesicle was imaged using three lasers (488 nm, 543 nm, 633 nm) on the CLSM. The three images are stills (proceeding in time from left to right, as indicated by the timestamp).
Figure 14:
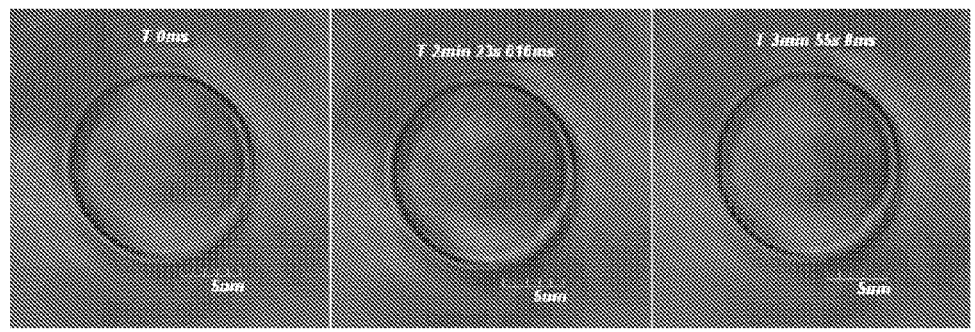
FIG. 14 illustrates vesicles produced with 1.5 mg/mL BODIPY-labeled HSAF, no $PZn_2$ (488 nm, 543 nm, 633 nm laser).
Figure 15:
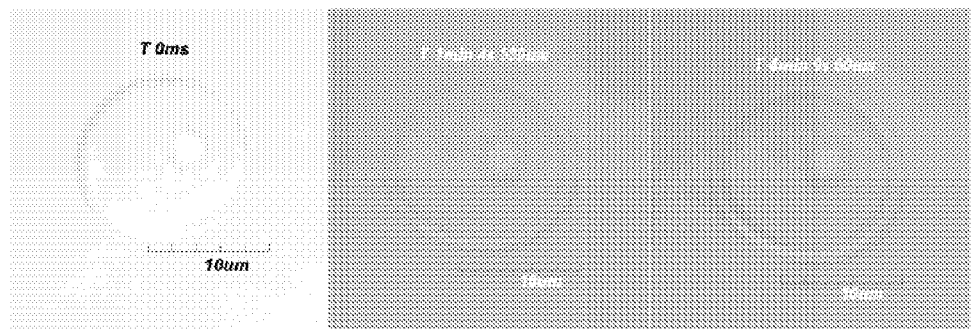
FIG. 15 illustrates vesicles produced with 1.5 mg/mL unlabeled HSAF, no $PZn_2$ (488 nm, 543 nm, 633 nm laser).
Figure 16G:
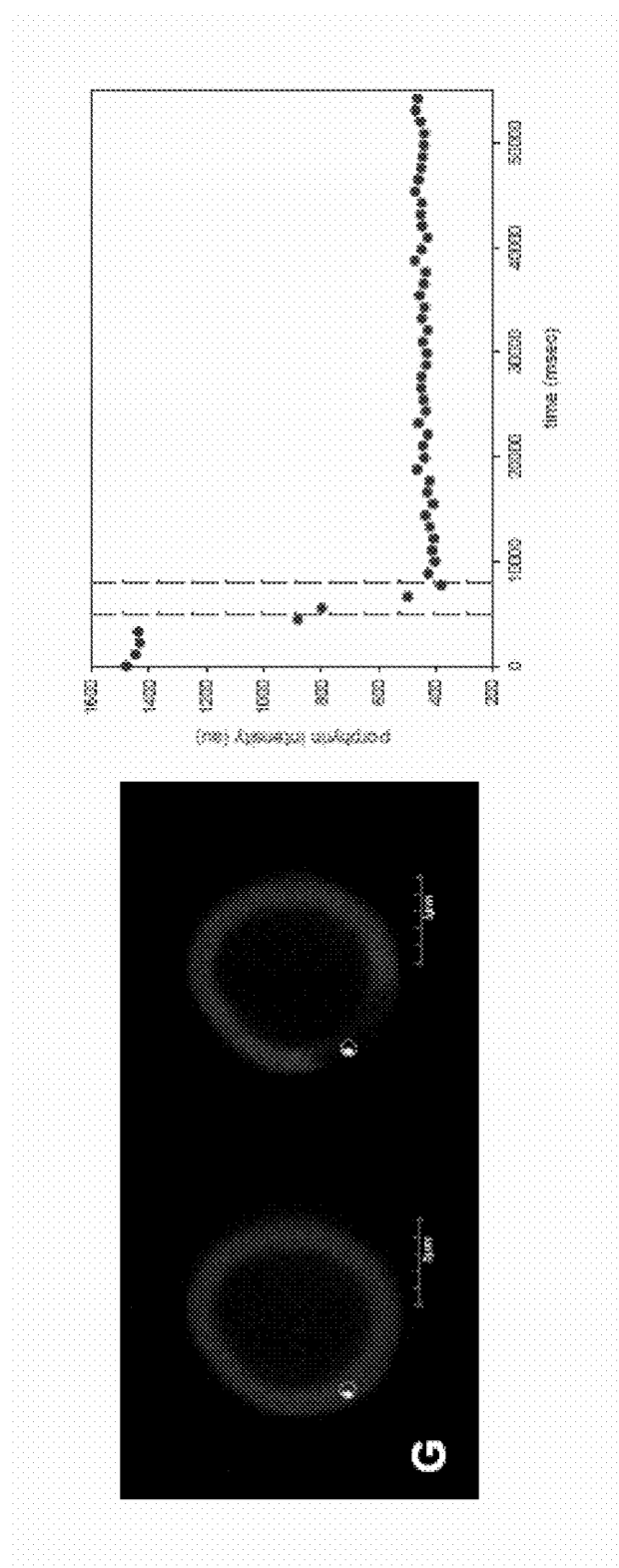
FIG. 16 illustrates FRAP results: pre-FRAP experiment and post-FRAP experiment image and corresponding fluorescent intensity versus time plots. All samples incorporate porphyrin su-PEG dimer in the membrane bilayer at 5:1 polymer:dye molar ratio and ferritin at 1.5 mg/mL in hydration solution. The samples tested incorporated HSF or HSAF labeled with BODIPY-FL or Cy3. (a) BODIPY-FL-apoferritin, membrane bleach (b) BODIPY-FL-ferritin, membrane bleach BODIPY-FL is used to label cysteine on the ferritin subunits (light gray); again, porphyrin su-peg dimer is loaded into the membrane bilayer (bright gray). Confocal microscopy reveals minimal ferritin in the aqueous core. FRAP measurements reveal minimal diffusion of ferritin at the membrane. These measurements support experiments performed using Cy3-labeled ferritin. (c) Cy3-apoferritin, membrane bleach (d) Cy3-apoferritin, aqueous core bleach (e) Cy3-ferritin, membrane bleach (f) Cy3-ferritin, aqueous core bleach (g) control (no ferritin), membrane bleach. Bleaching occurred during the time period within the vertical lines. Photobleaching was performed with a 351 nm laser. Cy3 is used to label lysine on the ferritin subunits (diffuse gray); this molecule has a net −1 charge. Porphyrin su-peg dimer is loaded into the membrane bilayer (bright gray). Confocal microscopy reveals Cy3-labeled ferritin in the aqueous core of the vesicles, and FRAP measurements show that ferritin is free to diffuse within the vesicle core. Ferritin and apoferritin are also imaged at the membrane, and FRAP measurements reveal minimal diffusion of ferritin at the membrane. These measurements suggest that ferritin, like the porphyrin dye, is trapped within the vesicle membrane.

Dynamic Light Scattering (DLS). Vesicles were prepared as described previously and sized by passing colloidal solutions twenty times through polycarbonate extrusion membranes with pore sizes of 5 μm, 1 μm, or 400 nm. Flow cytometry was performed on the samples, and size distributions of the remaining colloidal solutions were determined using DLS. Vesicles were mixed well in low-volume disposable cuvettes using a pipette. Three runs of 13-15 measurements on a Zetasizer Nano-S Instrument (Malvern Instruments, Southborough, Mass.) were performed. The results of these runs were averaged using accompanying DTS software (Malvern Instruments, Southborough, Mass.), and intensity transformations were used to determine particle size distribution. Distributions were normalized by dividing each intensity percentage by the highest value within the sample. The results are illustrated in FIG. 8.

Example 9

Dextran Vesicle Preparation

Materials. Two molecular weight polyethylene oxide-polybutadiene diblock copolymers (PEO$_{30}$-PBD$_{46}$, denoted OB29 and PEO$_{80}$-PBD$_{125}$, denoted OB18) were purchased from Polymer Source, Inc (Montreal, Quebec, Canada). A molecular weight series of dextran (*Leuconostoc mesenteroides* and *Leuconostoc* spp.), fluorescein isothiocyanate (FITC) labeled dextran (5000 MW), and phosphate buffered saline (PBS) tablets were purchased from SIGMA-ALDRICH (St. Louis, Mo.). Methylene chloride (HPLC grade) and sucrose were purchased from Fisher Chemicals (Pittsburgh, Pa.). The meso-to-meso ethyne bridged (porphinato)zinc(II) dimer (PZn$_2$) and trimer (PZn$_3$) were synthesized in the Therien laboratory following methodology and photo physical characterization previously described. Duncan, T. V., et al., *J. Am. Chem. Soc.*, 2006, 128(28), 9000-1.

Vesicle Preparation The Near Infra Red fluorophore, porphyrin (PZn$_2$), was dissolved in methylene chloride and added to the diblock copolymer PEO$_{30}$-b-PBD$_{46}$ (MW=3800 g mol$^{-1}$) at a 7.64M:1 M ratio. The resulting solution was uniformly coated on the rough side of a Teflon strip and the solvent was evaporated for >24 h. A 10 mg/mL dextran-sucrose solution was created by dissolving dextran of the desired MW in 2 mL of sucrose solution (290 milliosmolar). After hydration of the polymer-porphyrin film with the dextran-sucrose solution, the system was heated at 60° C. for >24 h and vortexed, resulting in spontaneous budding of giant NIR emissive polymersomes off the Teflon into the surrounding aqueous solution. The resulting giant polymersomes contained porphyrin loaded in the membrane (7.64:1 molar ratio of polymer to porphyrin) and dextran loaded in the aqueous core of the polymersomes (10 mg/mL). Vesicles were separated from free dextran by dilution of polymersomes in PBS. The diluted polymersome sample was placed in a centrifuge tube which contained a cushion of sucrose buffer+density gradient medium and was spun (20,000 rpm, 1 h, 4° C.) to separate the vesicles. The separated vesicles were then dialyzed into PBS (290 mOsm, 12 h, 4° C.).

Example 10

Rupture and Release of Dextran Encapsulated Polymersomes Confocal laser scanning microscopy (CLSM) was used to expose dextran polymersomes to light at wavelengths of 458, 488, 543, and 633 nm for 3 min. An Olympus Fluoview FV1000 confocal microscope (Center Valley, Pa.) with a UPLFLN 40× oil objective lens was used to image the vesicles with a scan speed of 2.0 µs/pixel (2.213 s/frame) for a total time of 3 min 26 ms. The resulting membrane rupture and deformation of the polymersome sample that occurred during this time was observed and the percent of polymersomes that deformed in for a given molecular weight dextran (n=3) was recorded.

Figure 17:
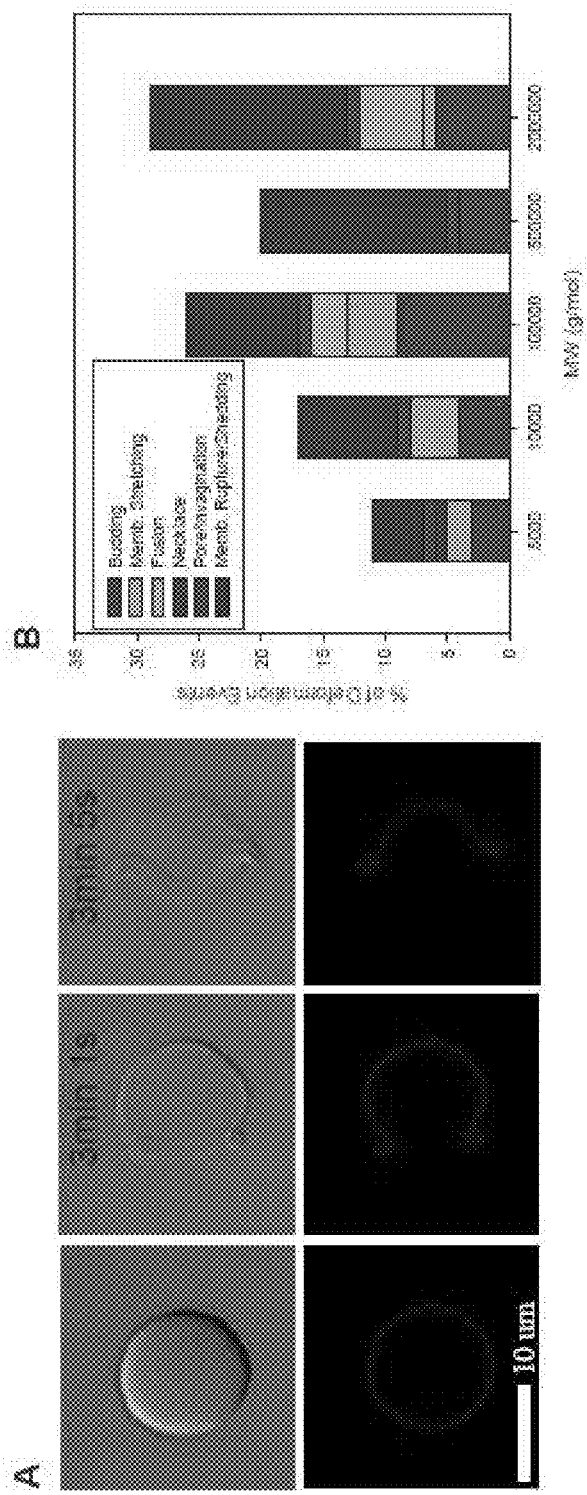
FIG. 17 illustrates membrane deformation of polymersome upon exposure to lasers. (A) Membrane rupture of a dextran-encapsulated polymersome upon exposure to lasers is the most common type of deformation that occurred. (B) Distribution of types of polymersome deformation that occur for each MW of dextran encapsulated.

Vesicle Deformation. Polymersomes with porphyrin encapsulated in the membrane and dextran encapsulated in the core deformed when exposed to confocal lasers 458, 488, 543, and 633 nm. The type of deformation ranged from membrane budding, pearl-like necklace formation, membrane stretching (toroidal), to membrane shedding and membrane rupture. The shedding and rupture were the most frequent types of deformation observed (51% of all deformation events) in polymersomes that deformed and often followed a curling trajectory as seen in FIG. 17A. Any budding or membrane stretching occurred during the first few seconds of light exposure while membrane rupture and shedding would occur across a wider distribution of time. Membrane shedding and rupture events made up more of the deformation events as the MW of dextran increased (FIG. 17B). Membrane rupture also occurred more frequently in unilamellar vesicles, opposed to the multilamellar vesicles that frequently form in the polymersome sample. This suggests that the membrane stress that leads to rupture or shedding is mitigated by the availability of excess membrane.

Modification of Dextran and Polymer. Increasing the MW of dextran resulted in a trend of increasing the frequency of deformation for polymersomes made from both OB29 and OB18 (FIG. 18A). Dextran has been shown to increase in amphiphilic behavior with increasing MW as it moves from a hydrophilic polysaccharide at lower MWs (1000) to becoming more hydrophobic at increasing MWs. In addition, increasing the MW of dextran leads to the formation of hydrophobic aggregates that occur at critical aggregation concentrations that drop as the MW of dextran increases Vieira, N. A. B., et al., *Carbohydrate Polymers*, 2002, 53, 137-143. Thus, the increasingly amphiphilic and aggregation behavior of dextran with increasing MW is likely the cause of the increasing frequency of deformation. There is a lower limit to the deformation as 1000 MW dextran encapsulation does not result in polymersome deformation in OB29 vesicles.

Figure 18:
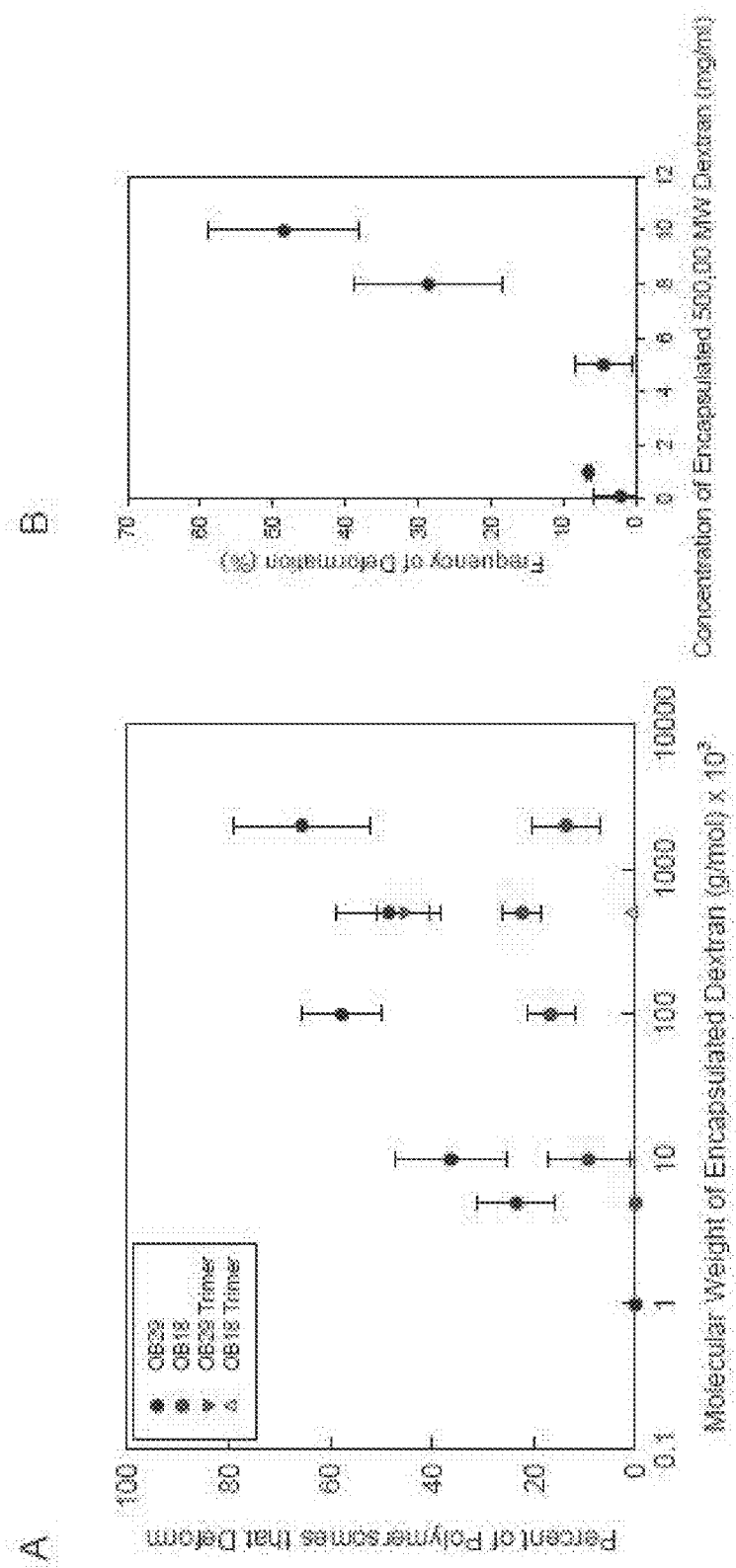
FIG. 18 illustrates the effect of dextran molecular weight on polymersome deformation. (A) Increasing the MW of dextran results in increasing the percent of polymersomes that deform during laser exposure for polymersomes made from both OB29 and OB18. Deformation of OB18 polymersomes requires a higher MW dextran and occurs less frequently than OB29 polymersomes. (B) A minimum concentration of dextran is required for deformation to occur.

When the di-block copolymer is changed from OB29 (3.6 kg/mol) to the higher MW and more rigid OB18 (10.4 kg/mol), the resulting polymersomes still deform, but at a significantly lower frequency. In addition, the lower limit to deformation again occurs, but is increased to 5000 MW dextran compared to OB29 vesicle's lower limit of 1000 MW dextran. Presumably, there is an upper limit to the MW of dextran, for both OB29 and OB18 vesicles, as well since the increasing hydrophobicity obstructs the self assembly of the bilayer leaflets. In addition to the lower limit of MW of dextran, there also is a lower limit on the dextran concentration (FIG. 18 B). While deformation occurs at a concentration of 10 mg/ml, this phenomena does not occur when the concentration is lowered to 1 mg/ml.

Example 11

Fluorescence Recovery After Photo Bleaching (FRAP) The Olympus Fluoview FV1000 confocal microscope, with 40× oil objective lens (described above) was used for the FRAP study. FITC conjugated dextran was encapsulated in the aqueous core of polymersomes that contained membrane encapsulated $PZn_2$. Two regions of the polymersome, at the membrane-core interface and in the center of the polymersomes, were chosen for imaging. Following a period of imaging, the selected region of the polymersome was photo bleached with 351 and 364 nm lasers at 80% power for 8 s. The polymersome area beyond the bleaching area was not imaged in order to reduce photo bleaching effects across the entire vesicle. The fluorescence intensities of the regions were tracked before, during, and after the bleaching using a 488 nm laser for FITC.

Figure 19:
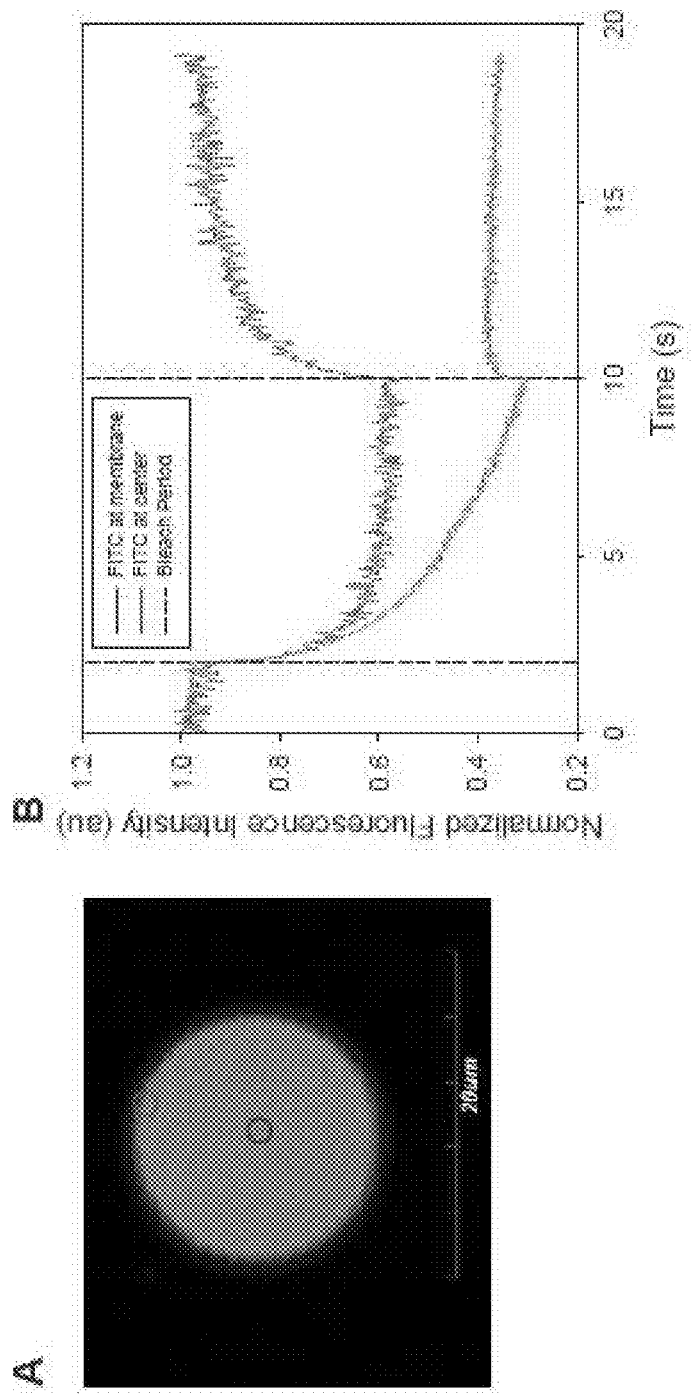
FIG. 19 illustrates fluorescence recovery after photobleaching (FRAP) of dextran encapsulated polymersomes (A) FITC-labeled dextran was encapsulated in the core of the polymersome (light gray) and $PZn_2$ was encapsulated in the membrane (dark gray). A region of the membrane (gray circle) and the aqueous core (black circle) were photobleached to assess diffusion of dextran. (B) Fluorescence recovery of FITC occurs after photobleaching (dark gray, upper line) in the center of the polymersome while fluorescence does not recover near the membrane (light gray, lower line).

Dextran Interaction with Membrane. To measure dextran mobility within and interaction with the polymersome membrane, fluorescence recovery after photobleaching (FRAP) experiments were performed. FITC tagged dextran was encapsulated in the core of polymersomes and two locations of the vesicle, near the membrane and at the center of the aqueous core, were photobleached (FIG. 19A). Previous studies have shown that $PZn_2$ dye motion within the membrane is restricted Robbins, G. P., et al., *J. Am. Chem. Soc.*, 2009, 131, 3872-3874.

In the current study, the mobility of dextran was observed to be restricted at the membrane, with no FITC fluorescence recovery after 8 s of photobleaching (FIG. 19B). No significant FITC recovery, however, was observed after photobleaching at the membrane, indicating very slow to no movement of dextran at the membrane. This immobility near the membrane indicated association of dextran with the membrane which was further explored through micropipette analysis of the mechanical properties of the membrane.

Example 12

Micropipet Aspiration

Mircopipet aspiration of polymersomes followed similar procedures to those described by Bermudez et al, *Macromolecules*, 2002, 35(21), 8203-8208. Briefly, micropipets made of borosilicate glass tubing (Griedrich and Dimmock, Milville, N.J.) were prepared using a needle/pipette puller (model 730, David Kopf Instruments, Tujunga, Calif.) and microforged using a glass bead to give the tip a smooth, flat edge. Inner diameters of pipettes used ranged from 5 to 7 µm and were measured using computer imaging software. Pipets were filled with PBS solution and connected to an aspiration station mounted on the side of a Zeiss inverted microscope, equipped with a manometer, Validyne pressure transducer (models DP 15-32 and DP 103-14, Validyne Engineering Corp., Northridge, Calif.), digital pressure read-outs, micromanipulators (model WR-6, Narishige, Tokyo, Japan), and MellesGriot millimanipulators (course x,y,z contro). Suction pressure was applied via a syringe connected to the manometer. Both dextran encapsulated and unloaded vesicles were picked up by the micropipets and pressure was increased stepwise in 2-5 cmH2O increments. The membrane was allowed 10 s after each pressure change to equilibrate. The resulting membrane extensions and membrane diameter were measured with ImageJ software and used to calculate the area expansion modulus (Ka) of the different polymersomes.

Micropipet Aspiration of Dextran Loaded Polymersomes

Figure 20:
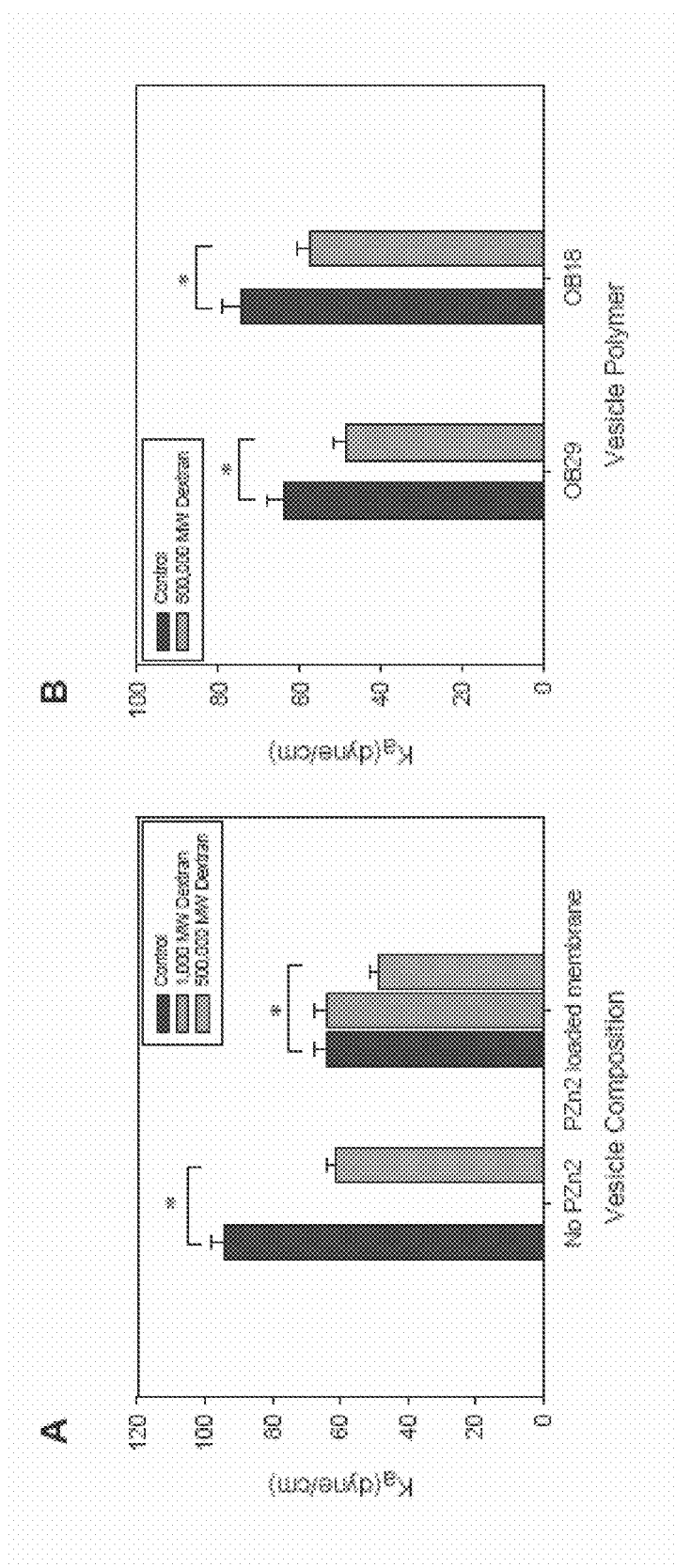
FIG. 20 illustrates the effect of dextran on membrane mechanical strength. (A) Dextran Encapsulation results in a significant decrease in the area expansion modulus (Ka) of polymersomes for both membranes without $PZn_2$ ($p=6.7E-6$) and in polymersomes membranes containing $PZn_2$ ($p=0.006$). Encapsulation of 1000 MW dextran, which does not result in deformation, does not significantly change the Ka of the membrane. (B) Dextran encapsulation significantly decreases the Ka of the higher molecular weight (and more rigid) OB18 polymersomes ($p=1.9E-2$). The resulting dextran encapsulated OB18 polymersome has a significantly higher Ka ($p=0.05$) than dextran encapsulated OB29 polymersomes.

In order to examine the interaction of dextran with the membrane, we studied the effect of dextran encapsulation on the mechanical properties of membrane. Specifically, the effect of Dextran MW on mechanical strength was studied. Encapsulation of 500,000 MW dextran, that successfully caused deformation in around 50% of vesicles exposed to light, resulted in a decrease in area elastic modulus (Ka) (FIG. 20 A). Encapsulation of 1000 MW dextran, which did not cause deformation, did not change the Ka. As a control, vesicles without $PZn_2$ were also studied to verify that the decrease in Ka was due to dextran, not the membrane encapsulated dye. FIG. 20 B shows the Ka analysis of dextran encapsulation in different polymer vesicles. The OB18 vesicle, which has previously been shown to be more rigid than OB29, does, in fact, have a greater Ka than OB29 (maroon bars). Upon dextran encapsulation, the Ka of OB18 vesicles similarly decreases, but also remains higher than dextran encapsulated OB29 vesicles.

The fact that the stress-strain behavior of the membrane is altered by the presence of dextran suggests that the polysaccharide interacts substantially with the membrane in ways sufficient to affect the mechanical properties. This change in mechanical properties rules out the possibility that the interaction of dextran with the membrane is merely physisorption on the exterior PEO corona. Rather, the data suggest that the amphiphilic saccharide penetrates the corona, at least to the point of the PEO-PBD interface. Incorporation of the dextran at this interface would reduce the interfacial tension, thereby affecting the Ka Santore, M. M., et al., *Langmuir*, 2002, 14, 2385-2395.

Figure 21C:
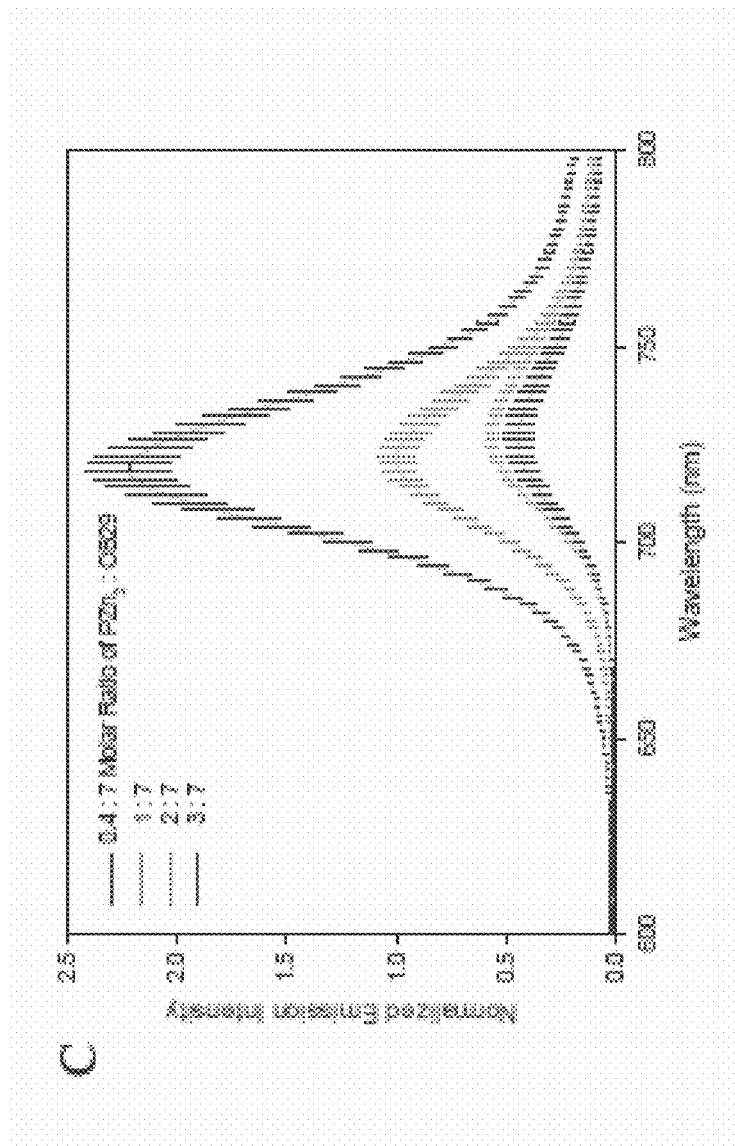
FIG. 21 illustrates the effect of increasing loading of $PZn_2$ in the membrane. (A) Increasing the concentration of $PZn_2$ in the membrane results in a decrease in frequency of polymersome deformation for polymersomes encapsulating 500,000 MW dextran. (B) Polymersome membranes do not experience a significant change in rigidity of their membranes with increasing amounts of $PZn_2$. (C) Fluorescence emission of $PZn_2$ decreases from polymersomes as loading is increased displaying a self-quenching phenomena between $PZn_2$ molecules.

Role of $PZn_2$ To investigate the role of porphyrin in the photo-activated polymersome deformation, porphyrin was loading was varied in the membrane and the resulting frequency of deformation assessed. Increasing the loading of $PZn_2$ from a 1:7 molar ratio of $PZn_2$ to OB29 to a 2:7 and 3:7 molar ratio results in a decreasing frequency of polymersome deformation (FIG. 21A). To determine if the cause of decreased frequency of deformation was an increased membrane rigidity induced by increased loading of $PZn_2$, micropipette analysis of the polymersomes was conducted. Micropipette results revealed no significant change in the Ka of the membranes implying no mechanical change of the membranes result due to increased $PZn_2$ loading (FIG. 21B). Fluorescence emission studies were then conducted to ensure differential loading of $PZn_2$ and begin to investigate possible non-radiative energy changes in the membrane. As $PZn_2$ loading is increased in the membrane, the dye emission decreases (FIG. 5C). This decrease in emission shows that porphyrin molecules self quench as they are loaded in higher concentrations and thus, come in close contact in the membrane. Previous studies have shown that $PZn_2$ loading as low as 1 M $PZn_2$: 20 M OB29 polymer results in self quenching (Ghoroghchian, P. P., et al., *Chem Mater*, 2007, 19(6), 1309-1318.)

Figure 22:
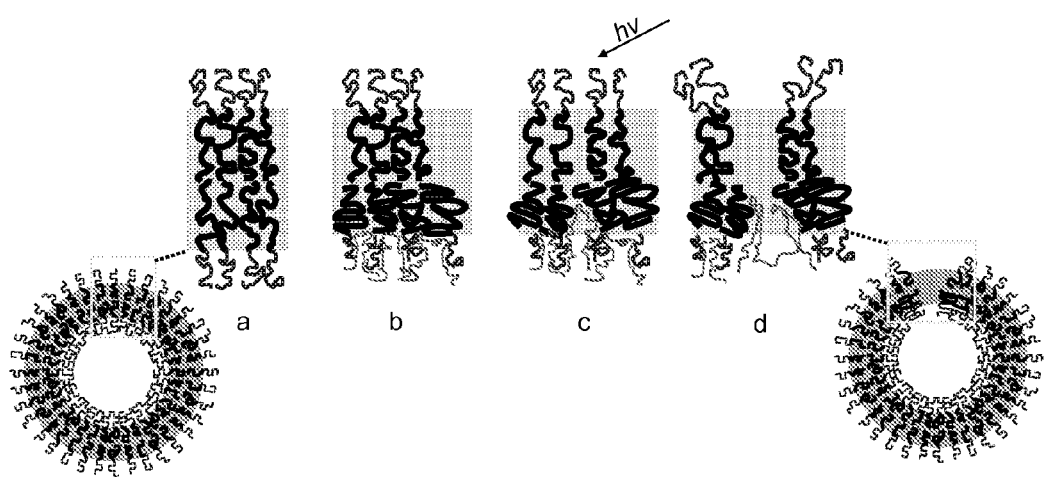
FIG. 22 illustrates a schematic of proposed photo activated polymersome deformation. (a) Polymersome membranes without encapsulant have chains that balance interfacial tension and chain entropy to exist in a semi-coiled state (b) Dextran penetration into corona reduces interfacial tension and causes further coiling of chains (c) Excess area is created in inner leaflet changing spontaneous curvature and thermal activation initiates the formation of a hole, stabilized by dextran (d) Continued localized heating by porphyrin initiates pore growth which reduces spontaneous curvature. Pore growth without self healing of polymer results in membrane bursting and curling.

Fluorescence emission begins to converge at higher loadings of 2:7 and 3:7 molar ratios of $PZn_2$ to OB29. This plateau in emission is likely the result of reaching the upper limit of $PZn_2$ membrane loading. The combined results of reaching the limit of membrane loading and the increased self quenching between $PZn_2$ show that $PZn_2$ molecules are in very close contact and in high amounts in the membrane. Currently, the role of porphyrin is proposed to be a localized producer of heat, due to $PZn_2$ low quantum yield (16%). As self-quenching effects usually result in an increase in non-radiative energy production (ie. heat), increased loading is expected to increase deformation by increasing heat production. The high level of $PZn_2$ packing, however, may likely act to deter deformation by allowing $PZn_2$ molecules, which have strong hydrophobic associations with the Pbd-PEO interface, to stabilize the membrane. Moving in the opposite direction, decreasing the loading of $PZn_2$ below a 1:7 Molar ratio also results in a decrease in the frequency of polymersome deformation. These two limits of porphyrin loading demonstrate there is a balance between $PZn_2$ induced heat production and $PZn_2$ induced membrane stabilization. Based on the above results, a schematic of the mechanism of deformation is proposed (FIG. 22).

When ranges are used herein for physical properties, such as molecular weight, or chemical properties, such as chemical formulae, all combinations and subcombinations of ranges specific embodiments therein are intended to be included.

The disclosures of each patent, patent application and publication cited or described in this document are hereby incorporated herein by reference, in its entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed:

1. A vesicle for intracorporeal administration comprising:
    an encapsulating polymer membrane surrounding a lumen and having an inner leaflet;
    a radio frequency absorptive moiety either forming part of the membrane or attached or conjugated to the membrane external to the lumen of the vesicle;
    said vesicle further comprising apoferritin in the lumen of the vesicle and associated with the inner leaflet of the membrane; and
    a therapeutic or diagnostic cargo in the lumen of the vesicle.

2. The vesicle of claim 1 further comprising at least one targeting moiety on the membrane external to the lumen.

3. The vesicle of claim 1 wherein the radiofrequency absorptive moiety is a porphyrin.

4. The vesicle of claim 1 wherein the polymer membrane comprises an amphiphilic block copolymer comprising at least one hydrophilic polymer bonded to at least one hydrophobic polymer.

5. A composition for intracorporeal administration comprising:
    A vesicle having:
        a) an encapsulating polymer membrane surrounding a lumen and having an inner leaflet;
        b) a radio frequency absorptive moiety either forming part of the membrane or attached or conjugated to the membrane external to the lumen of the vesicle;
        c) said vesicle further comprising protein apoferritin in the lumen of the vesicle and associated with the inner leaflet of the membrane; and
        d) a therapeutic or diagnostic cargo in the lumen of the vesicle; and
        e) a pharmaceutically acceptable carrier or diluent.

6. The composition of claim 5, wherein the vesicle further comprises at least one targeting moiety on the membrane external to the lumen.

7. The vesicle of claim 1, wherein the block copolymer is a polyethyleneoxide-polybutadiene block copolymer.

8. The vesicle of claim 1, wherein the block copolymer is a polyethyleneoxide-polycaprolactone block copolymer.

9. The vesicle of claim 8, wherein the polyethyleneoxide-polycaprolactone block copolymer is crosslinked.

10. The vesicle of claim 9, wherein the polyethyleneoxide-polycaprolactone block copolymer is chemically crosslinked.

11. The vesicle of claim 10, wherein the polyethyleneoxide-polycaprolactone block copolymer is chemically crosslinked by associating avidin with biotin attached to a terminal end of a polyethyleneoxide portion of the polyethyleneoxide-polycaprolactone block copolymer.

12. The vesicle of claim 7, wherein the polyethyleneoxide-polybutadiene block copolymer is crosslinked.

13. The vesicle of claim 12, wherein the polyethyleneoxide-polybutadiene block copolymer is chemically crosslinked.

14. The vesicle of claim 13, wherein the polyethyleneoxide-polybutadiene block copolymer is chemically crosslinked by associating avidin with biotin attached to a terminal end of a polyethyleneoxide portion of the polyethyleneoxide-polybutadiene block copolymer.

\* \* \* \* \*